United States Patent [19]

Ueki et al.

[11] Patent Number: 5,747,327
[45] Date of Patent: May 5, 1998

[54] PHOSPHOLIPASE D GENE ORIGINATED FROM PLANT

[75] Inventors: Jun Ueki; Shinji Morioka, both of Shizuoka, Japan

[73] Assignee: Japan Tobacco Inc., Tokyo, Japan

[21] Appl. No.: 446,794

[22] PCT Filed: Sep. 30, 1994

[86] PCT No.: PCT/JP94/01627

§ 371 Date: Jul. 26, 1995

§ 102(e) Date: Jul. 26, 1995

[87] PCT Pub. No.: WO95/09234

PCT Pub. Date: Apr. 6, 1995

[30] Foreign Application Priority Data

Sep. 30, 1993 [JP] Japan ..................... 5-267884

[51] Int. Cl.⁶ ............... C12N 1/20; C12N 9/20; C07H 21/04; C12P 21/06
[52] U.S. Cl. ............ 435/252.3; 536/23.6; 536/23.1; 435/198; 435/197; 435/195; 435/69.1; 435/320.1; 435/91.53
[58] Field of Search ............ 536/23.6, 23.1; 435/6, 7.6, 18, 69.1, 91.51, 91.53, 198, 195, 197

[56] References Cited

FOREIGN PATENT DOCUMENTS

| | | |
|---|---|---|
| 504869 | 9/1992 | European Pat. Off. . |
| 3-187382 | 8/1991 | Japan . |
| 04222527 | 8/1992 | Japan . |
| 5-76357 | 3/1993 | Japan . |
| WO94/00977 | 1/1994 | WIPO . |

OTHER PUBLICATIONS

Hayashi et al, Derwent WPI, EP 504869 (Sep. 23, 1992).
Derwent WPI, JP 04222527 (Aug. 12, 1992).
Wang et al. (1944). J. Biol. Chem. 269(32): 20312–20317 Aug. 12, 1994.
Takano et al, J. Jpn. Soc. Food Sci. Technol., vol. 34, No. 1, pp. 8–13 (1987).
Lee, Plant Science, vol. 59, pp. 25–33 (1989).
Brauer et al, Plant Physiol., vol. 92, pp. 672–678 (1990).
Abousalham et al, Biochimica et Biophysica Acta, vol. 1158, pp. 1–7 (1993).
Annual Mtg. of the American Society of Plant Physiologists, Pittsburgh, PA, Aug. 1–5, 1992, Abstract 447.
J. Biochem. 83, 677–680 (1978).
The Journal of Biological Chemistry, vol. 252, No. 3 pp. 1102–1106, 1977.
Plant Science, 59 (1989) 25–33.
Biochimica et Biophysica Acta, 369 (1974) 397–410.
Nippon Shokuhin Kogyo Gakkaishi vol. 34, No. 1, 8–13 (1987).
Journal of Bacteriology, Mar. 1990, pp. 1256–1261, vol. 172, No. 3.
Lambrecht, Romy and Ulbrich–Hofmann, Renate. Fachbereich Biochemie/Biotechnologie, Institut fur Biochemie, vol. 373 (1992).

*Primary Examiner*—Robert A. Wax
*Assistant Examiner*—Tekchand Saidha
*Attorney, Agent, or Firm*—Birch, Stewart, Kolasch & Birch LLP

[57] ABSTRACT

A cloned DNA encoding phospholipase D originated from a plant and a cloned DNA which regulates expression of phospholipase D gene originated from a plant are disclosed.

23 Claims, No Drawings

PHOSPHOLIPASE D GENE ORIGINATED FROM PLANT

TECHNICAL FIELD

The present invention relates to a phospholipase D gene originated from a plant.

BACKGROUND ART

Phospholipase D (hereinafter also referred to as "PLD") is one of phospholipid-decomposing enzymes, which catalyzes, for example, the reaction of decomposing lecithin to liberate phosphatidic acid and choline. This enzyme is known to occur in plants, animals and microorganisms. PLD is used as a reagent for measuring phospholipids in blood, as well as for hydrolysis of phospholipids and for production of derivatives by a base-exchange reaction utilizing the reversible reaction by PLD.

Purification and partial purification of PLDs originated from plants have been reported. That is, purification of rice PLD (Men Hui Lee, 1989, Phospholipase D of rice bran, I, purification and characterization, Plant Science 59, 25–33); partial purification of rice PLD (Katsumi TAKANO, Ikuzo KAMOI and Tetsujiro OBARA, 1987, About separation and purification, and properties of rice bran phospholipase D, J. Jpn. Soc. Food Sci. Technol., 34, 8–13 (1987)); purification of peanuts PLD (Michael Heller, Nava Mozes, Irena Peri and Eddie Maes, 1974, Phospholipase D from peanut seeds, IV, Final purification and some properties of the enzyme, Biochem. Biophys, Acta 369, 397–410); and purification of cabbage PLD (Romy Lambrecht and Renate Ulbrich-Hofmann, 1992, A facile purification procedure of phospholipase D from cabbage and its characterization, Biol. Chem. Hoppeseyler 373(2), 81–88) have been reported. However, amino acid sequences of plant PLDs have not been reported at all and genetical analyses thereof have also not been reported.

On the other hand, analyses of PLD genes of microorganisms and animals have been reported (Japanese Laid-open Patent Application (Kokai) No. 3-187382; Adrian L. M. Hodgson, Phillip Bird, and Ian T. Nisbet 1990, Cloning, nucleotide sequence, and expression in *Escherichia coli* of the phospholipase D gene from *Corynebacterium pseudotuberculosis*, Journal of Bacteriology 172, 1256–1261; and Japanese Laid-open Patent Application (Kokai) No. 5-76357).

If a PLD gene originated from a plant were available, the PLD originated from the plant may be produced in a large scale by a genetic engineering process, which is industrially advantageous. However, as mentioned above, since the amino acid sequence and DNA sequence of plant PLD have not been reported, it has hitherto been impossible to genetically manipulate the PLD gene. Further, as mentioned above, although the amino acid sequences and DNA sequences of PLDs of microorganisms and animals have been reported, since homologies of sequences are not observed among the PLD genes of microorganisms or among the PLD genes of microorganisms and animals, it is difficult to isolate plant PLD gene based on the reported information. Further, since there is no information about plant PLD gene, an antisense DNA which suppresses expression of the plant PLD gene has not been obtained.

DISCLOSURE OF THE INVENTION

An object of the present invention is to provide a PLD gene originated from a plant. Another object of the present invention is to provide an antisense DNA which can suppress the expression of the above-mentioned PLD gene according to the present invention. Still another object of the present invention is to provide a DNA which regulates expression of the PLD gene originated from a plant.

After intensive study, the present inventors succeeded in isolation of rice PLD gene and in sequencing the PLD gene by purifying PLD from rice, determining the partial amino acid sequence thereof, screening a rice cDNA library using as a probe the PCR product obtained by using the oligonucleotides encoding the above-mentioned partial amino acid sequence, cloning the inserted gene of positive clones and sequencing the inserted gene. Further, the present inventors succeeded in obtaining a cDNA clone of maize PLD using as a probe the DNA encoding rice PLD, and in sequencing the maize PLD gene. The present inventors still further succeeded in isolating a genome DNA clone carrying the regulatory sequence of rice PLD gene and in sequencing it.

That is, the present invention provides a DNA encoding phospholipase D originated from a plant. The present invention also provides a DNA which regulates the expression of phospholipase D gene originated from a plant.

By the present invention, a PLD gene originated from a plant was cloned for the first time. By using the DNA according to the present invention, the PLD originated from a plant, which is industrially useful, can be produced in a large scale by a genetic engineering process. Further, by the present invention, a DNA which regulates expression of the PLD gene originated from a plant was cloned for the first time. By virtue of this, expression of lipid-related genes may be suppressed, thereby modifying plant lipids.

BEST MODE FOR CARRYING OUT THE INVENTION

As mentioned above, the DNA according to the present invention encodes PLD originated from a plant. In the examples hereinbelow described, the DNA encoding rice PLD was isolated and sequenced. The deduced amino acid sequence encoded by the thus sequenced DNA is shown in SEQ ID NO. 2 in the Sequence Listing. The experimentally determined nucleotide sequence encoding the amino acid sequence shown in SEQ ID NO. 2 is shown in SEQ ID NO. 1. Therefore, the amino acid sequence shown in SEQ ID NO. 1 is identical to the amino acid sequence shown in SEQ ID NO. 2. Further, in the examples hereinbelow described, a cDNA clone of maize PLD gene was isolated using as a probe the thus sequenced DNA encoding the rice PLD and the maize PLD gene was sequenced. The deduced amino acid sequence encoded by the thus sequenced DNA is shown in SEQ ID NO. 4 in the Sequence Listing. The experimentally determined nucleotide sequence encoding the amino acid sequence shown in SEQ ID NO. 4 is shown in SEQ ID NO. 3. Therefore, the amino acid sequence shown in SEQ ID NO. 3 is identical to the amino acid sequence shown in SEQ ID NO. 4.

Further, in the examples described below, rice cDNA library was screened using as a probe the thus obtained DNA encoding rice PLD and positive clones were isolated, followed by sequencing the inserted DNA to obtain a clone carrying an inserted DNA having the nucleotide sequence shown in SEQ ID NO. 5. In SEQ ID NO. 5, the 1876th base is "A" which is the first "A" in the translation initiation codon ATG of the PLD structural gene, and the region upstream of the "A" (i.e., 1-1875nt) is thought to be a regulatory region of the PLD gene. The amino acid sequence encoded by the region downstream of 1876nt is interrupted by introns.

The DNA according to the present invention may be obtained by, for example, the method described in the examples below in which rice or maize is used as the starting material. Alternatively, since the nucleotide sequence of the gene was disclosed by the present invention, the PLD gene may easily be prepared by PCR method using as primers a pair of oligonucleotides each of which hybridizes with the respective end of the DNA according to the present invention and using the genome DNA of rice or maize as a template.

A plant producing PLD may be obtained by inserting the DNA encoding PLD originated from a plant according to the present invention into a vector for plants by a conventional method and transforming a plant with the obtained recombinant vector by a conventional method.

By inserting the DNA according to the present invention into a vector for plants in the reverse direction, an antisense DNA of PLD gene may be obtained. By transforming a plant with such a recombinant vector, the mRNA which hybridizes with the mRNA formed by transcription of the PLD gene intrinsic to the plant is produced, so that expression of the PLD gene intrinsic to the plant may be suppressed. If this technique is applied to a rice plant, a rice plant in which expression of PLD gene is suppressed is obtained, so that the taste of the rice is improved.

The DNA regulating the PLD gene originated from a plant according to the present invention may be used in combination with the antisense DNA of the PLD gene. By this, the antisense DNA can be expressed at the same place as the place in which the PLD gene intrinsic to the plant is expressed.

It is well-known in the art that there are cases wherein the activity of an enzyme is retained even if the amino acid sequence of an enzyme is modified to a small extent, that is, even if one or more amino acids in the amino acid sequence are substituted or deleted, or even if one or more amino acids are added to the amino acid sequence. DNAs encoding the proteins having such modifications and having PLD activity are included within the scope of the present invention. That is, cloned DNAs encoding amino acid sequences having the same amino acid sequence as SEQ ID NO. 2 or SEQ ID NO. 4 except that one or more amino acids are substituted, deleted or added, which give the enzyme activity of PLD, are also included in the scope of the present invention. Similarly, DNAs having the same nucleotide sequence as SEQ ID NO. 5 except that one or more nucleotides are substituted, deleted or added, which regulate expression of the DNA encoding the amino acid sequence giving the enzyme activity of PLD are also included within the scope of the present invention.

Modification of DNA which brings about addition, deletion or substitution of the amino acid sequence encoded thereby can be attained by the site-specific mutagenesis which is well-known in the art (e.g., Nucleic Acid Research, Vol. 10, No. 20, p6487–6500, 1982). In the present specification, "one or more amino acids" means the number of amino acids which can be added, deleted or substituted by the site-specific mutagenesis.

Site-specific mutagenesis may be carried out by, for example, using a synthetic oligonucleotide primer complementary to a single-stranded phage DNA except that the desired mutation as follows. That is, using the above-mentioned synthetic oligonucleotide as a primer, a complementary chain is produced by a phage, and host bacterial cells are transformed with the obtained double-stranded DNA. The culture of the transformed bacterial cells is plated on agar and plaques are formed from a single cell containing the phage. Theoretically, 50% of the new colonies contain the phage having a single-stranded chain carrying the mutation and remaining 50% of the colonies contain the phage having the original sequence. The obtained plaques are then subjected to hybridization with a kinase-treated synthetic probe at a temperature at which the probe is hybridized with the DNA having exactly the same sequence as the DNA having the desired mutation but not with the original DNA sequence that is not completely complementary with the probe. Then the plaques in which the hybridization was observed are picked up, cultured and the DNA is collected.

In addition to the above-mentioned site-specific mutagenesis, the methods for substituting, deleting or adding one or more amino acids without losing the enzyme activity include a method in which the gene is treated with a mutagen and a method in which the gene is selectively cleaved, a selected nucleotide is removed, added or substituted and then the gene is ligated.

EXAMPLES

The present invention will now be described more concretely by way of examples. However, the present invention is not restricted to the examples described below.

1. Purification of rice bran PLD

For the purification, a reference relating to the purification of rice bran PLD (Takano et al., J. Jpn. Soc. Food Sci. Technol., 34, 8–13 (1987)) was referred. The enzyme activity was measured by using phosphatidylcholine as the substrate and by quantifying the choline generated by the enzyme reaction by the choline oxidase method (Imamura et al., J. Biochem. 83, 677–680 (1978)). The enzyme reaction, however, was stopped by heat treatment at 95° C. for 5 minutes.

That is, one liter of hexane was added to 100 g of rice bran of *Oryza sativa* variety "Koshihikari" and the mixture was stirred overnight to defat the rice bran. Then 10 g of POLYCRAL AT (trademark: polyvinylpyrrolidone commercially available from GAF Chemical) and 500 ml of 10 mM Tris-HCl buffer (pH 7) containing 1 mM $CaCl_2$ and 5 mM 2-mercaptoethanol were added and the resulting mixture was stirred for one hour to extract enzyme. The extract was filtered through 8-ply gauze and the filtrate was centrifuged at 15,000×g for 20 minutes. The intermediate layer was collected as a crude extract. The crude extract was treated with ammonium sulfate (65% saturation) and formed precipitates were collected by centrifugation (15,000×g, 20 minutes). The precipitates were dissolved and dialyzed against the above-described buffer. After the dialysis, precipitates were removed by centrifugation to obtain a ammonium sulfate fraction.

The ammonium sulfate fraction was applied to a DEAE-Cellulose (commercially available from Whattman) column (2.0×10 cm) equilibrated with buffer A (10 mM Tris-HCl pH 7, 1 mM $CaCl_2$, 1 mM 2-mercaptoethanol). After washing the column with about 100 ml of buffer A containing 50 mM having linear gradient of NaCl from 50 to 350 mM. PLD was eluted in the vicinity of 0.2M of NaCl. The fractions exhibiting PLD activity were collected as an eluted solution (DEAE-Cellulose).

To the eluted solution (DEAE-Cellulose), 3M of ammonium sulfate was added to a concentration of 1M and the resultant was applied to a Phenyl Sepharose column (commercially available from PHARMACIA, 2.6×10 cm). Then the column was subjected to elution with 240 ml of buffer A having a gradient of ammonium sulfate from 1.0 to 0M. PLD was eluted in the vicinity of 0.1M of ammonium sulfate. Fractions exhibiting PLD activity were collected and dialyzed against buffer A to obtain an eluted solution (Phenyl Sepharose).

The eluted solution (Phenyl Sepharose) was applied to a Mono Q column (anion-exchange column, commercially available from PHARMACIA, 16×10 cm) and then elution was carried out with 150 ml of buffer A having a gradient of NaCl from 50–350 mM. PLD was eluted at NaCl concentrations from 210 mM to 235 mM. The fractions exhibiting PLD activity were collected and dialyzed against buffer A to obtain an eluted solution (Mono Q 1st).

The eluted solution (Mono Q 1st) was concentrated to 0.5 ml by centrifugal ultrafiltration and the resultant was applied to Superose 6 column (commercially available from PHARMACIA, 1.0–30 cm) equilibrated with buffer A containing 0.1M NaCl, and the column was subjected to elution with the same buffer. The molecular weight of the PLD was estimated as 78 kDa. The fractions exhibiting PLD activity were collected as an eluted solution (Superose 6).

To the eluted solution (Superose 6), 2.5 ml of 40% CARRIER AMPHOLITE (commercially available from PHARMACIA, pH 4.0–6.0) and distilled water were added to a final volume of 50 ml. The resultant was then subjected to isoelectric focusing using Rotofore (commercially available from BIORAD). The electrophoresis was carried out at 2° C. under a constant power of 12W for 4 hours. PLD activity was observed in the vicinity of pH4.9. The fractions exhibiting PLD activity were collected and the obtained solution was dialyzed against buffer A to obtain an isoelectric focusing fraction.

The isoelectric focusing fraction was applied to a Mono Q column (commercially available from PHARMACIA, 0.5×5 cm) and elution was carried out using buffer A having a linear gradient of NaCl from 50 mM to 350 mM. PLD was eluted in the vicinity of 210 mM and 235 mM NaCl. The two fractions exhibiting PLD activity were collected as eluted solutions (Mono Q 2nd-I and Mono Q 2nd-II).

Purities of the eluted solutions (Mono Q 2nd-I and Mono Q 2nd-II) were determined by SDS-polyacrylamide gel electrophoresis (Laemmli (1970)). After the electrophoresis, the gels were stained with COOMASSIE BRILLIANT BLUE R250. With either eluted solution, a main band was observed at the position of molecular weight of 82 kDa. A single band was observed with eluted solution (Mono Q 2nd-II).

By the above-described purification, eluted solutions (Mono Q 2nd-I and Mono Q 2nd-II) were 380-fold and 760-fold purified, respectively, based on the crude extract.

The two fractions were analyzed for properties of the enzymes contained therein. The results are shown in Table 1. The buffer solutions used for measuring the optimum pH were sodium acetate (pH4–6), MES-NaOH (pH5.5–7.0) and Tris-HCl (pH7–9), all of which had a concentration of 100 mM. The pH stability means the range in which decrease in activity was not observed after leaving the enzyme to stand at 25° C. for 30 minutes. The temperature stability was measured by measuring remaining activity after leaving the enzyme to stand at 4° C., 25° C., 37° C. or 50° C. for 30 minutes. The substrate specificity was measured at a substrate concentration of 5 mM and is expressed as a relative activity taking the enzyme activity to phosphatidylcholine as 100.

TABLE 1

|  | Mono Q 2nd-I | Mono Q 2nd-II |
|---|---|---|
| Km Value | 0.29 mM | 0.29 mM |
| Optimum pH | 6 | 6 |
| pH Stability | 7–8 | 7–8 |
| Temperature Stability | 4–37° C. | 4–37° C. |
| $Ca^{2+}$ Dependency | 20 mM or more | 20 mM or more |
| Substrate Specificity |  |  |
| Phosphatidylcholine | 100 | 100 |
| Lysophosphatidylcholine | 13 | 12 |
| Sphingomyelin | 6 | 4 |

2. Proof that Purified Protein is PLD

In the same manner as in the determination of the purity, eluted solutions (Mono Q 2nd-I and Mono Q 2nd-II) were separately subjected to SDS-polyacrylamide gel electrophoresis and each of the gels was transcribed to a PVDF membrane (commercially available from MILLIPORE), followed by staining the membrane. The band corresponding to the protein having a molecular weight of 82 kDa was cut out and amino acid sequence of the N-terminal region of the protein was determined. Amino acid sequence up to 10th amino acid residue was able to be determined for both proteins, and both proteins had the same sequence as follows:

Val Gly Lys Gly Ala Thr Lys Val Tyr Ser

Although the relationship between the proteins of 82 kDa which existed in two fractions having the enzyme activity was unknown, at least the homology of the amino acid sequences thereof was thought to be high. Thus, it was thought that there was no problem even if a mixture of these fractions was used as an antigen for producing an antibody.

A mixture of the eluted solutions (Mono Q 2nd-I and Mono Q 2nd-II) was subjected to SDS-polyacrylamide gel electrophoresis employing 7.5% acrylamide and the gel was stained with COOMASSIE BRILLIANT BLUE R250. The band containing the protein of 82 kDa was cut out and the proteins were recovered by electroelution (25 mM Tris, 192 mM glycine, 0.025% SDS, 100V, 10 hours). After removing SDS by electrodialysis (15 mM ammonium bicarbonate, 200V, 5 hours), the resultant was freeze-dried. The electroelution and electrophoresis were performed by using BIOTRAP (commercially available from SCHLEICHER & SCHUELL).

Rabbits were immunized with the protein of 82 kDa highly purified by the above-described method. Immunization was performed by administering 50 μg of the protein per time at 7 days' interval. Using blood serum before the immunization and after the third immunization, immunotitration was performed. That is, PLD solution containing $8.6×10^{-3}$ units of the enzyme, 0 to 50 μl of the serum before the immunization or after the third immunization, 50 μl of 250 mM Tris-HCl (pH 7.0), 5 μl of 50 mM $CaCl_2$, 50 μl of 0.2% TRITON X-100 (trademark) and balance of water were mixed to a final volume of 250 μl and the mixture was left to stand at room temperature for 2.5 hours. To the resulting mixture, 200 μl of Protein A SEPHAROSE (commercially available from PHARMACIA) was added and the resultant was gently shaken at room temperature for 2 hours. The resultant was centrifuged (500×g, 5 minutes) and enzyme activity of the supernatant was measured. Taking the enzyme activity when no serum was added as 100%, the enzyme activities measured when 20 μl or 50 μl of the serum before the immunization were 95% and 88%, respectively, while the enzyme activities measured when 20

μl or 50 μl of the serum after the third immunization were 75% and 30%, respectively. These results proved that the protein of 82 kDa is PLD.

3. Determination of Internal Amino Acid Sequence

The PLD protein was fragmented by fragmenting the protein in a gel (Cleveland et al., J. Biol. Chem., 252, 1102(1977)). The gel containing the PLD protein, which was cut out by the same method as described in 2 was inserted in a stacking gel well on a 15% acrylamide gel prepared for separation of peptides. *Staphylococcus aureus* V8 protease (commercially available from WAKO PURE CHEMICAL INDUSTRIES, LTD) in an amount of 1/10 of the PLD protein was overlaid and electrophoresis was started. The electrophoresis was interrupted when bromophenol blue reached the center of the stacking gel, and 30 minutes after, the electrophoresis was restarted. After the electrophoresis, the gel was transcribed to a PVDF membrane and the PVDF membrane was stained. Clear bands were observed at positions corresponding to molecular weights of 20, 14, 13, 11 and 10 kDa. The bands corresponding to molecular weights of 20, 14 and 13 kDa were cut out and amino acid sequences of the peptide fragments contained in the bands were determined by a protein sequencer. The sequences are as follows:

20 kDa: Asn Tyr Phe His Gly Ser Asp Val Asn ? Val Leu ? Pro Arg Asn Pro Asp Asp(Asp) ? ? Ile 14 kDa: Thr ? Asn Val Gln Leu Phe Arg Ser Ile Asp Gly Gly Ala Ala Phe Gly Phe Pro Asp Thr Pro Glu Glu Ala Ala Lys ? Gly Leu Val Ser Gly 13 kDa: Ile Ala Met Gly Gly Tyr Gln Phe Tyr His Leu Ala Thr Arg Gln Pro Ala Arg Gly Gln Ile His Gly Phe Arg Met Ala Leu ? Tyr Glu His Leu Gly Met Leu ? Asp Val Phe (In the sequences, "?" means the residue which could not be identified and the amino acid residue in parenthesis is one which may be another amino acid residue with a considerable probability.)

4. Preparation of cDNA Library of Rice Immature Seeds

Total RNAs were prepared from immature seeds 5 days after blossom by extracting RNAs by the SDS-phenol method and by precipitating the extract with lithium chloride. Poly(A) +RNAs were prepared using OLIGOTEX-dT30 (commercially available from TAKARA SHUZO) in accordance with the instructions by the manufacturer. For cDNA cloning, cDNA SYNTHESIS SYSTEM PLUS (commercially available from AMERSHAM) and cDNA CLONING SYSTEM λgt10 (commercially available from AMERSHAM) were used. As the cloning vector, λZAPII vector (commercially available from STRATAGENE) was used and as the host cells, XL1-Blue was used.

5. Preparation of Probes

Oligonucleotides corresponding to the amino acid sequence of PLD were synthesized by a DNA synthesizer (commercially available from APPLIED BIOSYSTEMS). The sequences thereof and the amino acid sequences corresponding thereto are described below.

20KF: 5'AAYTAYTTYCAYGG 3'

20KR1: 5'RTCRTCRTCNGGRTT 3'

(wherein R represents purine bases, that is, A or G; Y represents pyrimidine bases, that is, T or C; and N represents G, A, T or C.)

20KF is a mixture of 32 types of oligonucleotides each of which encodes the amino acid sequence of Asn Tyr Phe His Gly that was found in the peptide having a molecular weight of 20 kDa, and 20KR1 is a mixture of 128 types of oligonucleotides each of which encodes the amino acid sequence of Asn Pro Asp Asp (Asp)

that was found in the same peptide.

The cDNA synthesis reaction was carried out in a mixture of 10 ng of Poly(A)+RNA, 0.3 μg of random hexamer (dN6), 10 U of RNase inhibitor (RNAGuard, commercially available from PHARMACIA), 1 mM each of dATP, dCTP, dGTP and dTTP, 1×PCR buffer (commercially available from TAKARA SHUZO), 50 mM of magnesium chloride and 100 U of reverse transcriptase (M-MuLV RTase, commercially available from BRL), the total volume of the reaction mixture being 10 μl. The reaction was carried out at 37° C. for 30 minutes and the mixture was then heated at 95° C. for 5 minutes, followed by retaining the resulting mixture in ice.

Polymerase chain reaction (PCR) was performed using the above-described cDNA as a template, and 20KF and 20KR1 as primers. The reaction was carried out using 10 μl of the cDNA synthesis reaction mixture, a mixture of 50 pmol each of the primers, 200 μM each of dATP, dCTP, dGTP and dTTP, 1×PCR buffer (commercially available from TAKARA SHUZO) and 2.5 U of AmpliTaq DNA polymerase (commercially available from TAKARA SHUZO), the total volume of the reaction mixture being 50 μl. A cycle of 94° C. for 1 minute/40° C. for 1 minute/72° C. for 2.5 minutes was repeated 30 times in DNA THERMOCYCLER (commercially available from PERKIN ELMER CETUS).

PCR product was separated on 2% agarose gel. Several fragments were detected by staining the gel with ethidium bromide. One of them had a size of 94 bp which is the expected size.

The PCR fragment was cut out from the gel and subcloned into pUC19 plasmid. The subcloned PCR fragment was sequenced by the dideoxy method using T7 sequencing kit (commercially available from PHARMACIA). Between the two primers, a nucleotide sequence encoding the expected amino acid sequence was observed. The nucleotide sequence between the two primers and the amino acid sequence encoded thereby are as follows:

C TCT GAC GTG AAC TGT GTT CTA TGC CCT CGC
Ser Asp Val Asn Cys Val Leu Cys Pro Arg

Isotope $^{32}$P (commercially available from AMERSHAM) was incorporated into the above-described oligonucleotide using DNA 5'-end labelling kit MEGALABEL (commercially available from TAKARA SHUZO) to obtain a radioactive oligonucleotide probe.

6. Screening of PLD Gene-containing Clone

Using the above-described radioactive oligonucleotide as a probe, a cDNA library was screened. The hybridization solution was 0.5M sodium phosphate buffer (pH 7.2) containing 7% SDS, 1 mM EDTA and 100 μg/ml of salmon sperm DNA, and hybridization was carried out at 45° C. for 16 hours after adding the probe to this solution. The washing solution contained 0.3M NaCl and 30 mM sodium citrate and washing was performed twice at 45° C. for 20 minutes. Positive plaques were isolated and subcloned in vivo into pBluescript plasmid (commercially available from STRATAGENE) in accordance with the instruction of the manufacturer of λZAPII cloning vector. The nucleotide sequence was determined and the region encoding the internal amino acid sequence determined in 3 existed.

7. Sequencing of 5'-end Region

Since a clone containing the full-length cDNA could not be isolated, a DNA fragment containing the 5'-end region was prepared by RACE method (Edwards et al., Nucleic Acids Res., 19, 5227–5232(1991)). 5'-AmpliFINDER RACE Kit (commercially available from CLONETECH)

was used in accordance with the instructions attached to the product. OligoDNAs were prepared and PCR was performed using the mRNA prepared by the method described in 4 as a template. The PCR product was subcloned into PCRII vector (commercially available from INVITROGEN) and sequenced by the dideoxy method. As a result, it was estimated that translation is initiated from the 182th nucleotide shown in SEQ ID NO. 1 because a termination codon exists upstream thereof by 36 bp.

8. Preparation of cDNA Clone Encoding PLD Originated from Maize

Maize cDNA clone was obtained by the method described below using the DNA encoding rice PLD as a probe.

Using suspended cultured cells established by culturing a callus derived from immature embryo of maize inbred Mo 17(commercially available from MIKE BRAYTON SEEDS, INC.) in a liquid culture medium, a cDNA library was prepared by the method described in 4. However, λgt10 vector (commercially available from AMERSHAM) was used as the cloning vector and NM-514 (commercially available from AMERSHAM) was used as the host cells. Using the cDNA of rice PLD as a probe, positive plaques were isolated by the method described in 6. Phage DNA was prepared in accordance with the instructions by the manufacturer of the cloning vector. The phage DNA was digested with a restriction enzyme Kpn I and the resultant was subcloned into pBluescript plasmid. The nucleotide sequence was determined by the dideoxy method as described in 6.

9. Isolation of PLD Genome Clone Corresponding to PLD cDNA and Identification of Promoter Region To isolate a genomic DNA clone carrying the regulatory sequence of the PLD gene corresponding to the PLD cDNA sequenced in 6, which was cloned into pBluescript plasmid, a genomic library of rice Koshihikari was prepared. This was carried out by partially digesting DNAs from leaves of Koshihikari with Mbo I, purifying fractions having sizes of 16–20 kb by sucrose gradient centrifugation, and by using lambda DASH II (commercially available from STRATAGENE) and GigapackII Gold (commercially available from STRATAGENE). Using the PLD cDNA clone as a probe, the genome library was screened. The screening was performed as described in 6. However, the hybridization was performed at 65° C. for 16 hours, the washing solution was 0.5×SSC containing 0.1% SDS and washing was performed twice at 65° C. for 20 minutes. The nucleotide sequence of the hybridized genome clone was determined by the dideoxy method. As a result, a region homologous to the cDNA sequence determined in 6 existed.

The transcription initiation site was determined by the method described in 7. In the vicinity of the transcription initiation site, "TATA" consensus sequence box was observed. The ATG translation initiation site was determined as the upstream most ATG codon in the translation reading frame of the clone and as the ATG codon which is first accessible in the mRNA synthesized in rice.

A part of the DNA sequence of the genome clone hybridized with the cDNA clone is shown in SEQ ID NO. 5. In the genome DNA sequence, a reading frame starting from the ATG translation initiation codon, which overlaps with the corresponding cDNA sequence, was identified. The promoter region is located upstream of the ATG translation initiation codon and starts immediately upstream thereof.

We claim:

1. A cloned DNA which encodes phospholipase D originated from a plant, wherein said DNA comprises a nucleotide sequence selected from the group consisting of nucleotides 182–2617 of SEQ ID NO:1 and nucleotides 107–2542 of SEQ ID NO:3 or a sequence complementary thereto or a sequence which specifically hybridizes to said cloned DNA or said complementary sequence in a hybridization solution containing 0.5M sodium phosphate buffer, pH 7.2, containing 7% SDS, 1 mM EDTA and 100 mg/ml of salmon sperm DNA at 65° C. for 16 hours and washing twice at 65° C. for twenty minutes in a washing solution containing 0.5×SSC and 0.1% SDS.

2. The DNA according to claim 1, which encodes phospholipase D originated from a monocotyledonous plant.

3. A cloned DNA which encodes an amino acid sequence shown in SEQ ID NO. 2 or an amino acid sequence having the same sequence as shown in SEQ ID NO. 2 except that one or more amino acids are added, deleted or substituted, said amino acid sequence giving enzyme activity of phospholipase D.

4. A cloned DNA which encodes the amino acid sequence shown in SEQ ID NO: 2.

5. A cloned DNA which encodes an amino acid sequence shown in SEQ ID NO. 4 or an amino acid sequence having the same sequence as shown in SEQ ID NO. 4 except that one or more amino acids are added, deleted or substituted, said amino acid sequence giving enzyme activity of phospholipase D.

6. A cloned DNA which comprises a nucleotide sequence shown in SEQ ID NO: 5.

7. The DNA according to claim 3, which has a nucleotide sequence shown in SEQ ID NO. 1 or has the same nucleotide sequence as shown in SEQ ID NO. 1 except that one or more nucleotides are added, deleted or substituted, said nucleotide sequence encodes an amino acid sequence giving enzyme activity of phospholipase D.

8. The DNA according to claim 7, which has a nucleotide sequence shown in SEQ ID NO. 1.

9. The DNA according to claim 5, which has a nucleotide sequence shown in SEQ ID NO. 3 or has the same nucleotide sequence as shown in SEQ ID NO. 3 except that one or more nucleotides are added, deleted or substituted, said nucleotide sequence encodes an amino acid sequence giving enzyme activity of phospholipase D.

10. The DNA according to claim 9, which has a nucleotide sequence shown in SEQ ID NO. 3.

11. The DNA according to claim 4, which has a nucleotide sequence from 182th to 2617th nucleotide in the nucleotide sequence shown in SEQ ID NO. 1.

12. The DNA according to claim 6, which has a nucleotide sequence from 107th to 2542th nucleotide in the nucleotide sequence shown in SEQ ID NO. 3.

13. A cloned DNA which regulates expression of phospholipase D gene originated from a plant.

14. A cloned DNA which has a nucleotide sequence shown in SEQ ID NO. 5 or has the same nucleotide sequence as shown in SEQ ID NO. 5 except that one or more nucleotides are added, deleted or substituted, said nucleotide sequence regulates expression of the DNA encoding an amino acid sequence giving enzyme activity of phospholipase D.

15. A cloned DNA which comprises a nucleotide sequence shown in SEQ ID NO: 5.

16. A cloned DNA which comprises a nucleotide sequence from 1st to 1875th nucleotide in the nucleotide sequence shown in SEQ ID NO: 5.

17. A cloned DNA which has a nucleotide sequence selected from the group consisting of SEQ ID NO: 1, SEQ ID NO: 3 and SEQ ID NO: 5 or a sequence complementary thereto or a DNA which specifically hybridizes to said cloned DNA or said complementary sequence in a hybridization solution containing 0.5M sodium phosphate buffer, pH 7.2, containing 7% SDS, 1 mM EDTA and 100 µg/ml of salmon sperm DNA at 45° C. or 65° C. for 16 hours and washing twice at 45° C. or 650° C. for twenty minutes in a washing solution containing 0.3M NaCl and 30 mM sodium citrate or in a washing solution containing 0.5×SSC containing 0.1% SDS.

18. An antisense polynucleotide which can suppress the expression of a DNA which encodes a phospholipase D originated from a plant, wherein said DNA has a nucleotide sequence selected from the group consisting of SEQ ID NO: 1, SEQ ID NO: 3 and SEQ ID NO: 5 or wherein said DNA specifically hybridizes to said antisense sequence in a hybridization solution containing 0.5M sodium phosphate buffer, pH 7.2, containing 7% SDS, 1 mM EDTA and 100 µg/ml of salmon sperm DNA, at 45° C. or 65° C. for 16 hours and washing twice at 45° C. or 65° C. for twenty minutes in a washing solution containing 0.3M NaCl and 30 mM sodium citrate or in a washing solution containing 0.5×SSC containing 0.1% SDS.

19. The cloned DNA of claim 17, wherein said plant is a rice plant.

20. The cloned DNA of claim 17, wherein said plant is a corn plant.

21. The cloned DNA of claim 17, which is a vector containing said DNA.

22. The cloned DNA of claim 17, which is a cloning vector containing said DNA.

23. A cell which contains the DNA of claim 17 or the vector of claim 21.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
( A ) LENGTH: 3040 base pairs
( B ) TYPE: nucleic acid
( C ) STRANDEDNESS: single
( D ) TOPOLOGY: linear ( i i ) MOLECULE TYPE: cDNA to mRNA ( i i i ) HYPOTHETICAL: NO ( i x ) FEATURE:
( A ) NAME/KEY: CDS
( B ) LOCATION: 182..2617

( x i ) SEQUENCE DESCRIPTION: SEQ ID NO:1:

```
AGTCTCTCTT    CTCCCGCAAT    TTTATAATCT    CGATCGATCC    AATCTGCTCC    CCTTCTTCTT          60

CTACTCTCCC    CATCTCGGCT    CTCGCCATCG    CCATCCTCCT    CTCCCTTCCC    GGAGAAGACG         120

CCTCCCTCCG    CCGATCACCA    CCCGGTAGGG    CGAGGAGGGA    GCCAAATCCA    AATCAGCAGC         180

C ATG GCG CAG ATG CTG CTC CAT GGG ACG CTG CAC GCC ACC ATC TTC                           226
  Met Ala Gln Met Leu Leu His Gly Thr Leu His Ala Thr Ile Phe
  1               5                   10                  15

GAG GCG GCG TCG CTC TCC AAC CCG CAC CGC GCC AGC GGA AGC GCC CCC                         274
Glu Ala Ala Ser Leu Ser Asn Pro His Arg Ala Ser Gly Ser Ala Pro
            20                  25                  30
```

-continued

| | | | | | | | | | | | | | | | | |
|---|---|---|---|---|---|---|---|---|---|---|---|---|---|---|---|---|
| AAG | TTC | ATC | CGC | AAG | TTT | GTG | GAG | GGG | ATT | GAG | GAC | ACT | GTG | GGT | GTC | 322 |
| Lys | Phe | Ile | Arg<br>35 | Lys | Phe | Val | Glu | Gly<br>40 | Ile | Glu | Asp | Thr | Val<br>45 | Gly | Val | |
| GGC | AAA | GGC | GCC | ACC | AAG | GTG | TAT | TCT | ACC | ATT | GAT | CTG | GAG | AAA | GCT | 370 |
| Gly | Lys | Gly<br>50 | Ala | Thr | Lys | Val | Tyr<br>55 | Ser | Thr | Ile | Asp | Leu<br>60 | Glu | Lys | Ala | |
| CGT | GTA | GGG | CGA | ACT | AGG | ATG | ATA | ACC | AAT | GAG | CCC | ATC | AAC | CCT | CGC | 418 |
| Arg | Val<br>65 | Gly | Arg | Thr | Arg | Met<br>70 | Ile | Thr | Asn | Glu | Pro<br>75 | Ile | Asn | Pro | Arg | |
| TGG | TAT | GAG | TCG | TTC | CAC | ATC | TAT | TGC | GCT | CAT | ATG | GCT | TCC | AAT | GTG | 466 |
| Trp<br>80 | Tyr | Glu | Ser | Phe | His<br>85 | Ile | Tyr | Cys | Ala | His<br>90 | Met | Ala | Ser | Asn | Val<br>95 | |
| ATC | TTC | ACT | GTC | AAG | ATT | GAT | AAC | CCT | ATT | GGG | GCA | ACG | AAT | ATT | GGG | 514 |
| Ile | Phe | Thr | Val | Lys<br>100 | Ile | Asp | Asn | Pro | Ile<br>105 | Gly | Ala | Thr | Asn | Ile<br>110 | Gly | |
| AGG | GCT | TAC | CTG | CCT | GTC | CAA | GAG | CTT | CTC | AAT | GGA | GAG | GAG | ATT | GAC | 562 |
| Arg | Ala | Tyr | Leu<br>115 | Pro | Val | Gln | Glu | Leu<br>120 | Leu | Asn | Gly | Glu | Glu<br>125 | Ile | Asp | |
| AGA | TGG | CTC | GAT | ATC | TGT | GAT | AAT | AAC | CGC | GAG | TCT | GTT | GGT | GAG | AGC | 610 |
| Arg | Trp | Leu | Asp<br>130 | Ile | Cys | Asp | Asn | Asn<br>135 | Arg | Glu | Ser | Val | Gly<br>140 | Glu | Ser | |
| AAG | ATC | CAT | GTG | AAG | CTT | CAG | TAC | TTC | GAT | GTT | TCC | AAG | GAT | CGC | AAT | 658 |
| Lys | Ile | His | Val | Lys<br>145 | Leu | Gln | Tyr | Phe | Asp<br>150 | Val | Ser | Lys | Asp | Arg<br>155 | Asn | |
| TGG | GCG | AGG | GGT | GTC | CGC | AGT | ACC | AAG | TAT | CCA | GGT | GTT | CCT | TAC | ACC | 706 |
| Trp<br>160 | Ala | Arg | Gly | Val | Arg<br>165 | Ser | Thr | Lys | Tyr | Pro<br>170 | Gly | Val | Pro | Tyr | Thr<br>175 | |
| TTC | TTC | TCT | CAG | AGG | CAA | GGG | TGC | AAA | GTT | ACC | TTG | TAC | CAA | GAT | GCT | 754 |
| Phe | Phe | Ser | Gln | Arg<br>180 | Gln | Gly | Cys | Lys | Val<br>185 | Thr | Leu | Tyr | Gln | Asp<br>190 | Ala | |
| CAT | GTC | CCA | GAC | AAC | TTC | ATT | CCA | AAG | ATT | CCG | CTT | GCC | GAT | GGC | AAG | 802 |
| His | Val | Pro | Asp<br>195 | Asn | Phe | Ile | Pro | Lys<br>200 | Ile | Pro | Leu | Ala | Asp<br>205 | Gly | Lys | |
| AAT | TAT | GAA | CCC | CAC | AGA | TGC | TGG | GAG | GAT | ATC | TTT | GAT | GCT | ATA | AGC | 850 |
| Asn | Tyr | Glu | Pro<br>210 | His | Arg | Cys | Trp | Glu<br>215 | Asp | Ile | Phe | Asp | Ala<br>220 | Ile | Ser | |
| AAT | GCT | CAA | CAT | TTG | ATT | TAC | ATC | ACT | GGC | TGG | TCT | GTA | TAC | ACT | GAG | 898 |
| Asn | Ala | Gln<br>225 | His | Leu | Ile | Tyr | Ile<br>230 | Thr | Gly | Trp | Ser | Val<br>235 | Tyr | Thr | Glu | |
| ATC | ACC | TTG | GTT | AGG | GAC | TCC | AAT | CGT | CCA | AAA | CCT | GGA | GGG | GAT | GTC | 946 |
| Ile<br>240 | Thr | Leu | Val | Arg | Asp<br>245 | Ser | Asn | Arg | Pro | Lys<br>250 | Pro | Gly | Gly | Asp | Val<br>255 | |
| ACC | CTT | GGG | GAG | TTG | CTC | AAG | AAG | AAG | GCC | AGT | GAA | GGT | GTT | CGG | GTC | 994 |
| Thr | Leu | Gly | Glu | Leu<br>260 | Leu | Lys | Lys | Lys | Ala<br>265 | Ser | Glu | Gly | Val | Arg<br>270 | Val | |
| CTC | ATG | CTT | GTG | TGG | GAT | GAC | AGG | ACT | TCA | GTT | GGT | TTG | CTA | AAG | AGG | 1042 |
| Leu | Met | Leu | Val<br>275 | Trp | Asp | Asp | Arg | Thr<br>280 | Ser | Val | Gly | Leu | Leu<br>285 | Lys | Arg | |
| GAT | GGC | TTG | ATG | GCA | ACA | CAT | GAT | GAG | GAA | ACT | GAA | AAT | TAC | TTC | CAT | 1090 |
| Asp | Gly | Leu | Met<br>290 | Ala | Thr | His | Asp | Glu<br>295 | Glu | Thr | Glu | Asn | Tyr<br>300 | Phe | His | |
| GGC | TCT | GAC | GTG | AAC | TGT | GTT | CTA | TGC | CCT | CGC | AAC | CCT | GAT | GAC | TCA | 1138 |
| Gly | Ser | Asp<br>305 | Val | Asn | Cys | Val | Leu<br>310 | Cys | Pro | Arg | Asn | Pro<br>315 | Asp | Asp | Ser | |
| GGC | AGC | ATT | GTT | CAG | GAT | CTG | TCG | ATC | TCA | ACT | ATG | TTT | ACA | CAC | CAT | 1186 |
| Gly | Ser | Ile | Val<br>320 | Gln | Asp | Leu | Ser | Ile<br>325 | Ser | Thr | Met | Phe<br>330 | Thr | His | His<br>335 | |
| CAG | AAG | ATA | GTA | GTT | GTT | GAC | CAT | GAG | TTG | CCA | AAC | CAG | GGC | TCC | CAA | 1234 |
| Gln | Lys | Ile | Val | Val<br>340 | Val | Asp | His | Glu | Leu<br>345 | Pro | Asn | Gln | Gly | Ser<br>350 | Gln | |

| | | | | | | | | | | | | | | | | |
|---|---|---|---|---|---|---|---|---|---|---|---|---|---|---|---|---|
| CAA | AGG | AGG | ATA | GTC | AGT | TTC | GTT | GGT | GGC | CTT | GAT | CTC | TGT | GAT | GGA | 1282 |
| Gln | Arg | Arg | Ile | Val | Ser | Phe | Val | Gly | Gly | Leu | Asp | Leu | Cys | Asp | Gly | |
| | | | 355 | | | | 360 | | | | | | 365 | | | |
| AGG | TAT | GAC | ACT | CAG | TAC | CAT | TCT | TTG | TTT | AGG | ACA | CTC | GAC | AGT | ACC | 1330 |
| Arg | Tyr | Asp | Thr | Gln | Tyr | His | Ser | Leu | Phe | Arg | Thr | Leu | Asp | Ser | Thr | |
| | | 370 | | | | | 375 | | | | | 380 | | | | |
| CAT | CAT | GAT | GAC | TTC | CAC | CAG | CCA | AAC | TTT | GCC | ACT | GCA | TCA | ATC | AAA | 1378 |
| His | His | Asp | Asp | Phe | His | Gln | Pro | Asn | Phe | Ala | Thr | Ala | Ser | Ile | Lys | |
| | 385 | | | | | 390 | | | | | 395 | | | | | |
| AAG | GGT | GGA | CCT | AGA | GAG | CCA | TGG | CAT | GAT | ATT | CAC | TCA | CGG | CTG | GAA | 1426 |
| Lys | Gly | Gly | Pro | Arg | Glu | Pro | Trp | His | Asp | Ile | His | Ser | Arg | Leu | Glu | |
| 400 | | | | | 405 | | | | | 410 | | | | | 415 | |
| GGG | CCA | ATC | GCA | TGG | GAT | GTT | CTT | TAC | AAT | TTC | GAG | CAG | AGA | TGG | AGA | 1474 |
| Gly | Pro | Ile | Ala | Trp | Asp | Val | Leu | Tyr | Asn | Phe | Glu | Gln | Arg | Trp | Arg | |
| | | | | 420 | | | | | 425 | | | | | 430 | | |
| AAG | CAG | GGT | GGT | AAG | GAT | CTC | CTT | CTG | CAG | CTC | AGG | GAT | CTG | TCT | GAC | 1522 |
| Lys | Gln | Gly | Gly | Lys | Asp | Leu | Leu | Leu | Gln | Leu | Arg | Asp | Leu | Ser | Asp | |
| | | | 435 | | | | | 440 | | | | | 445 | | | |
| ACT | ATT | ATT | CCA | CCT | TCT | CCT | GTT | ATG | TTT | CCA | GAG | GAC | AGA | GAA | ACA | 1570 |
| Thr | Ile | Ile | Pro | Pro | Ser | Pro | Val | Met | Phe | Pro | Glu | Asp | Arg | Glu | Thr | |
| | | 450 | | | | | 455 | | | | | 460 | | | | |
| TGG | AAT | GTT | CAG | CTA | TTT | AGA | TCC | ATT | GAT | GGT | GGT | GCT | GCT | TTT | GGG | 1618 |
| Trp | Asn | Val | Gln | Leu | Phe | Arg | Ser | Ile | Asp | Gly | Gly | Ala | Ala | Phe | Gly | |
| | 465 | | | | | 470 | | | | | 475 | | | | | |
| TTC | CCT | GAT | ACC | CCT | GAG | GAG | GCT | GCA | AAA | GCT | GGG | CTT | GTA | AGC | GGA | 1666 |
| Phe | Pro | Asp | Thr | Pro | Glu | Glu | Ala | Ala | Lys | Ala | Gly | Leu | Val | Ser | Gly | |
| 480 | | | | | 485 | | | | | 490 | | | | | 495 | |
| AAG | GAT | CAA | ATC | ATT | GAC | AGG | AGC | ATC | CAG | GAT | GCA | TAC | ATA | CAT | GCC | 1714 |
| Lys | Asp | Gln | Ile | Ile | Asp | Arg | Ser | Ile | Gln | Asp | Ala | Tyr | Ile | His | Ala | |
| | | | | 500 | | | | | 505 | | | | | 510 | | |
| ATC | CGG | AGG | GCA | AAG | AAC | TTC | ATC | TAT | ATA | GAG | AAC | CAA | TAC | TTC | CTT | 1762 |
| Ile | Arg | Arg | Ala | Lys | Asn | Phe | Ile | Tyr | Ile | Glu | Asn | Gln | Tyr | Phe | Leu | |
| | | | 515 | | | | | 520 | | | | | 525 | | | |
| GGA | AGT | TCC | TAT | GCC | TGG | AAA | CCC | GAG | GGC | ATC | AAG | CCT | GAA | GAC | ATT | 1810 |
| Gly | Ser | Ser | Tyr | Ala | Trp | Lys | Pro | Glu | Gly | Ile | Lys | Pro | Glu | Asp | Ile | |
| | | 530 | | | | | 535 | | | | | 540 | | | | |
| GGT | GCC | CTG | CAT | TTG | ATT | CCT | AAG | GAG | CTT | GCA | CTG | AAA | GTT | GTC | AGT | 1858 |
| Gly | Ala | Leu | His | Leu | Ile | Pro | Lys | Glu | Leu | Ala | Leu | Lys | Val | Val | Ser | |
| | 545 | | | | | 550 | | | | | 555 | | | | | |
| AAG | ATT | GAA | GCC | GGG | GAA | CGG | TTC | ACT | GTT | TAT | GTT | GTG | GTG | CCA | ATG | 1906 |
| Lys | Ile | Glu | Ala | Gly | Glu | Arg | Phe | Thr | Val | Tyr | Val | Val | Val | Pro | Met | |
| 560 | | | | | 565 | | | | | 570 | | | | | 575 | |
| TGG | CCT | GAG | GGT | GTT | CCA | GAG | AGT | GGA | TCT | GTT | CAG | GCA | ATC | CTG | GAC | 1954 |
| Trp | Pro | Glu | Gly | Val | Pro | Glu | Ser | Gly | Ser | Val | Gln | Ala | Ile | Leu | Asp | |
| | | | | 580 | | | | | 585 | | | | | 590 | | |
| TGG | CAA | AGG | AGA | ACA | ATG | GAG | ATG | ATG | TAC | ACT | GAC | ATT | ACA | GAG | GCT | 2002 |
| Trp | Gln | Arg | Arg | Thr | Met | Glu | Met | Met | Tyr | Thr | Asp | Ile | Thr | Glu | Ala | |
| | | | 595 | | | | | 600 | | | | | 605 | | | |
| CTC | CAA | GCC | AAG | GGA | ATT | GAA | GCG | AAC | CCC | AAG | GAC | TAC | CTC | ACT | TTC | 2050 |
| Leu | Gln | Ala | Lys | Gly | Ile | Glu | Ala | Asn | Pro | Lys | Asp | Tyr | Leu | Thr | Phe | |
| | | 610 | | | | | 615 | | | | | 620 | | | | |
| TTC | TGC | TTG | GGT | AAC | CGT | GAG | GTG | AAG | CAG | GCT | GGG | GAA | TAT | CAG | CCT | 2098 |
| Phe | Cys | Leu | Gly | Asn | Arg | Glu | Val | Lys | Gln | Ala | Gly | Glu | Tyr | Gln | Pro | |
| | 625 | | | | | 630 | | | | | 635 | | | | | |
| GAA | GAA | CAA | CCA | GAA | GCT | GAC | ACT | GAT | TAC | AGC | CGA | GCT | CAG | GAA | GCT | 2146 |
| Glu | Glu | Gln | Pro | Glu | Ala | Asp | Thr | Asp | Tyr | Ser | Arg | Ala | Gln | Glu | Ala | |
| 640 | | | | | 645 | | | | | 650 | | | | | 655 | |
| AGG | AGG | TTC | ATG | ATC | TAT | GTC | CAC | ACC | AAA | ATG | ATG | ATA | GTT | GAC | GAT | 2194 |
| Arg | Arg | Phe | Met | Ile | Tyr | Val | His | Thr | Lys | Met | Met | Ile | Val | Asp | Asp | |
| | | | | 660 | | | | | 665 | | | | | 670 | | |

| | | | | | | | | | | | | | | | |
|---|---|---|---|---|---|---|---|---|---|---|---|---|---|---|---|
| GAG | TAC | ATC | ATC | ATC | GGT | TCT | GCA | AAC | ATC | AAC | CAG | AGG | TCG | ATG | GAC |
| Glu | Tyr | Ile | Ile | Ile | Gly | Ser | Ala | Asn | Ile | Asn | Gln | Arg | Ser | Met | Asp |
| | | | 675 | | | | 680 | | | | | 685 | | | |

2242

| GGC | GCT | AGG | GAC | TCT | GAG | ATC | GCC | ATG | GGC | GGG | TAC | CAG | CCA | TAC | CAT |
|---|---|---|---|---|---|---|---|---|---|---|---|---|---|---|---|
| Gly | Ala | Arg | Asp | Ser | Glu | Ile | Ala | Met | Gly | Gly | Tyr | Gln | Pro | Tyr | His |
| | | 690 | | | | 695 | | | | 700 | | | | | |

2290

| CTG | GCG | ACC | AGG | CAA | CCA | GCC | CGT | GGC | CAG | ATC | CAT | GGC | TTC | CGG | ATG |
|---|---|---|---|---|---|---|---|---|---|---|---|---|---|---|---|
| Leu | Ala | Thr | Arg | Gln | Pro | Ala | Arg | Gly | Gln | Ile | His | Gly | Phe | Arg | Met |
| 705 | | | | | 710 | | | | | 715 | | | | | |

2338

| GCG | CTG | TGG | TAC | GAG | CAC | CTG | GGA | ATG | CTG | GAT | GAT | GTG | TTC | CAG | CGC |
|---|---|---|---|---|---|---|---|---|---|---|---|---|---|---|---|
| Ala | Leu | Trp | Tyr | Glu | His | Leu | Gly | Met | Leu | Asp | Asp | Val | Phe | Gln | Arg |
| 720 | | | | | 725 | | | | | 730 | | | | | 735 |

2386

| CCC | GAG | AGC | CTG | GAG | TGT | GTG | CAG | AAG | GTG | AAC | AGG | ATC | GCG | GAG | AAG |
|---|---|---|---|---|---|---|---|---|---|---|---|---|---|---|---|
| Pro | Glu | Ser | Leu | Glu | Cys | Val | Gln | Lys | Val | Asn | Arg | Ile | Ala | Glu | Lys |
| | | | | 740 | | | | | 745 | | | | | 750 | |

2434

| TAC | TGG | GAC | ATG | TAC | TCC | AGC | GAC | GAC | CTC | CAG | CAG | GAC | CTC | CCT | GGC |
|---|---|---|---|---|---|---|---|---|---|---|---|---|---|---|---|
| Tyr | Trp | Asp | Met | Tyr | Ser | Ser | Asp | Asp | Leu | Gln | Gln | Asp | Leu | Pro | Gly |
| | | | 755 | | | | 760 | | | | | 765 | | | |

2482

| CAC | CTC | CTC | AGC | TAC | CCC | ATT | GGC | GTC | GCC | AGC | GAT | GGT | GTG | GTG | ACT |
|---|---|---|---|---|---|---|---|---|---|---|---|---|---|---|---|
| His | Leu | Leu | Ser | Tyr | Pro | Ile | Gly | Val | Ala | Ser | Asp | Gly | Val | Val | Thr |
| | | 770 | | | | 775 | | | | 780 | | | | | |

2530

| GAG | CTG | CCC | GGG | ATG | GAG | TAC | TTT | CCT | GAC | ACA | CGG | GCC | CGC | GTC | CTC |
|---|---|---|---|---|---|---|---|---|---|---|---|---|---|---|---|
| Glu | Leu | Pro | Gly | Met | Glu | Tyr | Phe | Pro | Asp | Thr | Arg | Ala | Arg | Val | Leu |
| 785 | | | | | 790 | | | | | 795 | | | | | |

2578

| GGC | GCC | AAG | TCG | GAT | TAC | ATG | CCC | CCC | ATC | CTC | ACC | TCA | TAGACGAGGA |
|---|---|---|---|---|---|---|---|---|---|---|---|---|---|
| Gly | Ala | Lys | Ser | Asp | Tyr | Met | Pro | Pro | Ile | Leu | Thr | Ser | |
| 800 | | | | | 805 | | | | | 810 | | | |

2627

| AGCACTACAC | TACAATCTGC | TGGCTTCTCC | TGTCAGTCCT | TCTGTACTTC | TTCAGTTTGG | 2687 |
|---|---|---|---|---|---|---|
| TGGCGAGATG | GTATGGCCGT | TGTTCAGAAT | TCTTCAGAA | TAGCAGTTGT | TACAGTTGTG | 2747 |
| AATCATAAAG | TAATAAGTGC | AGTATCTGTG | CATGGTTGAG | TTGGGAAGAA | GATCGGGGAT | 2807 |
| GCAATGATGC | TTGTGAAGTT | GTGATGCCGT | TTGTAAGATG | GGAAGTTGGG | AACTACTAAG | 2867 |
| TAATTGGCAT | GATTGTACTT | TGCACTACTG | TTTAGCGTTG | TTGATACTGG | TTAACCGTGT | 2927 |
| GTTCATCTGA | ACTTGATTCT | TGATGCAGTT | TGTGGCATTA | CCAGTTTATC | ATCGTTCTTC | 2987 |
| AGGAAAAAAA | AAAAAAAAAA | AAAAAAAAAA | AAAAAAAAAA | AAAAAAAAAA | AAA | 3040 |

( 2 ) INFORMATION FOR SEQ ID NO:2:

( i ) SEQUENCE CHARACTERISTICS:
        ( A ) LENGTH: 812 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Ala | Gln | Met | Leu | Leu | His | Gly | Thr | Leu | His | Ala | Thr | Ile | Phe | Glu |
|---|---|---|---|---|---|---|---|---|---|---|---|---|---|---|---|
| 1 | | | | 5 | | | | | 10 | | | | | 15 | |

| Ala | Ala | Ser | Leu | Ser | Asn | Pro | His | Arg | Ala | Ser | Gly | Ser | Ala | Pro | Lys |
|---|---|---|---|---|---|---|---|---|---|---|---|---|---|---|---|
| | | | 20 | | | | | 25 | | | | | 30 | | |

| Phe | Ile | Arg | Lys | Phe | Val | Glu | Gly | Ile | Glu | Asp | Thr | Val | Gly | Val | Gly |
|---|---|---|---|---|---|---|---|---|---|---|---|---|---|---|---|
| | | 35 | | | | | 40 | | | | | 45 | | | |

| Lys | Gly | Ala | Thr | Lys | Val | Tyr | Ser | Thr | Ile | Asp | Leu | Glu | Lys | Ala | Arg |
|---|---|---|---|---|---|---|---|---|---|---|---|---|---|---|---|
| | 50 | | | | | 55 | | | | | 60 | | | | |

| Val | Gly | Arg | Thr | Arg | Met | Ile | Thr | Asn | Glu | Pro | Ile | Asn | Pro | Arg | Trp |
|---|---|---|---|---|---|---|---|---|---|---|---|---|---|---|---|
| 65 | | | | | 70 | | | | | 75 | | | | | 80 |

| Tyr | Glu | Ser | Phe | His | Ile | Tyr | Cys | Ala | His | Met | Ala | Ser | Asn | Val | Ile |
|---|---|---|---|---|---|---|---|---|---|---|---|---|---|---|---|
| | | | | 85 | | | | | 90 | | | | | 95 | |

-continued

| | | | | | | | | | | | | | | |
|---|---|---|---|---|---|---|---|---|---|---|---|---|---|---|
| Phe | Thr | Val | Lys<br>100 | Ile | Asp | Asn | Pro<br>105 | Ile | Gly | Ala | Thr | Asn<br>110 | Ile | Gly | Arg |
| Ala | Tyr | Leu<br>115 | Pro | Val | Gln | Glu<br>120 | Leu | Leu | Asn | Gly | Glu<br>125 | Ile | Asp | Arg |
| Trp | Leu<br>130 | Asp | Ile | Cys | Asp<br>135 | Asn | Asn | Arg | Glu | Ser<br>140 | Val | Gly | Glu | Ser | Lys |
| Ile<br>145 | His | Val | Lys | Leu | Gln<br>150 | Tyr | Phe | Asp | Val | Ser<br>155 | Lys | Asp | Arg | Asn | Trp<br>160 |
| Ala | Arg | Gly | Val | Arg<br>165 | Ser | Thr | Lys | Tyr | Pro<br>170 | Gly | Val | Pro | Tyr<br>175 | Thr | Phe |
| Phe | Ser | Gln | Arg<br>180 | Gln | Gly | Cys | Lys | Val<br>185 | Thr | Leu | Tyr | Gln | Asp<br>190 | Ala | His |
| Val | Pro | Asp<br>195 | Asn | Phe | Ile | Pro | Lys<br>200 | Ile | Pro | Leu | Ala | Asp<br>205 | Gly | Lys | Asn |
| Tyr | Glu<br>210 | Pro | His | Arg | Cys | Trp<br>215 | Glu | Asp | Ile | Phe | Asp<br>220 | Ala | Ile | Ser | Asn |
| Ala<br>225 | Gln | His | Leu | Ile | Tyr<br>230 | Ile | Thr | Gly | Trp | Ser<br>235 | Val | Tyr | Thr | Glu | Ile<br>240 |
| Thr | Leu | Val | Arg | Asp<br>245 | Ser | Asn | Arg | Pro | Lys<br>250 | Pro | Gly | Gly | Asp | Val<br>255 | Thr |
| Leu | Gly | Glu | Leu<br>260 | Leu | Lys | Lys | Lys | Ala<br>265 | Ser | Glu | Gly | Val | Arg<br>270 | Val | Leu |
| Met | Leu | Val<br>275 | Trp | Asp | Asp | Arg | Thr<br>280 | Ser | Val | Gly | Leu | Leu<br>285 | Lys | Arg | Asp |
| Gly | Leu<br>290 | Met | Ala | Thr | His | Asp<br>295 | Glu | Glu | Thr | Glu | Asn<br>300 | Tyr | Phe | His | Gly |
| Ser<br>305 | Asp | Val | Asn | Cys | Val<br>310 | Leu | Cys | Pro | Arg | Asn<br>315 | Pro | Asp | Asp | Ser | Gly<br>320 |
| Ser | Ile | Val | Gln | Asp<br>325 | Leu | Ser | Ile | Ser | Thr<br>330 | Met | Phe | Thr | His | His<br>335 | Gln |
| Lys | Ile | Val | Val<br>340 | Val | Asp | His | Glu | Leu<br>345 | Pro | Asn | Gln | Gly | Ser<br>350 | Gln | Gln |
| Arg | Arg | Ile<br>355 | Val | Ser | Phe | Val | Gly<br>360 | Gly | Leu | Asp | Leu | Cys<br>365 | Asp | Gly | Arg |
| Tyr | Asp<br>370 | Thr | Gln | Tyr | His | Ser<br>375 | Leu | Phe | Arg | Thr | Leu<br>380 | Asp | Ser | Thr | His |
| His<br>385 | Asp | Asp | Phe | His | Gln<br>390 | Pro | Asn | Phe | Ala | Thr<br>395 | Ala | Ser | Ile | Lys | Lys<br>400 |
| Gly | Gly | Pro | Arg | Glu<br>405 | Pro | Trp | His | Asp | Ile<br>410 | His | Ser | Arg | Leu | Glu<br>415 | Gly |
| Pro | Ile | Ala | Trp<br>420 | Asp | Val | Leu | Tyr | Asn<br>425 | Phe | Glu | Gln | Arg | Trp<br>430 | Arg | Lys |
| Gln | Gly | Gly<br>435 | Lys | Asp | Leu | Leu | Leu<br>440 | Gln | Leu | Arg | Asp | Leu<br>445 | Ser | Asp | Thr |
| Ile | Ile<br>450 | Pro | Pro | Ser | Pro | Val<br>455 | Met | Phe | Pro | Glu | Asp<br>460 | Arg | Glu | Thr | Trp |
| Asn<br>465 | Val | Gln | Leu | Phe | Arg<br>470 | Ser | Ile | Asp | Gly | Gly<br>475 | Ala | Ala | Phe | Gly | Phe<br>480 |
| Pro | Asp | Thr | Pro | Glu<br>485 | Glu | Ala | Ala | Lys | Ala<br>490 | Gly | Leu | Val | Ser<br>495 | Gly | Lys |
| Asp | Gln | Ile | Ile<br>500 | Asp | Arg | Ser | Ile | Gln<br>505 | Asp | Ala | Tyr | Ile | His<br>510 | Ala | Ile |
| Arg | Arg | Ala<br>515 | Lys | Asn | Phe | Ile | Tyr<br>520 | Ile | Glu | Asn | Gln | Tyr<br>525 | Phe | Leu | Gly |

Ser Ser Tyr Ala Trp Lys Pro Glu Gly Ile Lys Pro Glu Asp Ile Gly
    530             535             540
Ala Leu His Leu Ile Pro Lys Glu Leu Ala Leu Lys Val Val Ser Lys
545             550             555             560
Ile Glu Ala Gly Glu Arg Phe Thr Val Tyr Val Val Pro Met Trp
                565             570             575
Pro Glu Gly Val Pro Glu Ser Gly Ser Val Gln Ala Ile Leu Asp Trp
            580             585             590
Gln Arg Arg Thr Met Glu Met Met Tyr Thr Asp Ile Thr Glu Ala Leu
        595             600             605
Gln Ala Lys Gly Ile Glu Ala Asn Pro Lys Asp Tyr Leu Thr Phe Phe
    610             615             620
Cys Leu Gly Asn Arg Glu Val Lys Gln Ala Gly Glu Tyr Gln Pro Glu
625             630             635             640
Glu Gln Pro Glu Ala Asp Thr Asp Tyr Ser Arg Ala Gln Glu Ala Arg
            645             650             655
Arg Phe Met Ile Tyr Val His Thr Lys Met Met Ile Val Asp Asp Glu
                660             665             670
Tyr Ile Ile Ile Gly Ser Ala Asn Ile Asn Gln Arg Ser Met Asp Gly
        675             680             685
Ala Arg Asp Ser Glu Ile Ala Met Gly Gly Tyr Gln Pro Tyr His Leu
    690             695             700
Ala Thr Arg Gln Pro Ala Arg Gly Gln Ile His Gly Phe Arg Met Ala
705             710             715             720
Leu Trp Tyr Glu His Leu Gly Met Leu Asp Asp Val Phe Gln Arg Pro
            725             730             735
Glu Ser Leu Glu Cys Val Gln Lys Val Asn Arg Ile Ala Glu Lys Tyr
        740             745             750
Trp Asp Met Tyr Ser Ser Asp Asp Leu Gln Gln Asp Leu Pro Gly His
    755             760             765
Leu Leu Ser Tyr Pro Ile Gly Val Ala Ser Asp Gly Val Val Thr Glu
770             775             780
Leu Pro Gly Met Glu Tyr Phe Pro Asp Thr Arg Ala Arg Val Leu Gly
785             790             795             800
Ala Lys Ser Asp Tyr Met Pro Pro Ile Leu Thr Ser
            805             810

(2) INFORMATION FOR SEQ ID NO:3:

(i) SEQUENCE CHARACTERISTICS:
        (A) LENGTH: 2804 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (ix) FEATURE:
        (A) NAME/KEY: CDS
        (B) LOCATION: 107..2542

(xi) SEQUENCE DESCRIPTION: SEQ ID NO:3:

```
ATCACCGTCG TCATCAATCA CGGTGACCTT GCCCTCGCTG CCCGACTGGA ACCGGACGCT      60
GCTGCTGCTG GTAGGCTGAC AGCGAGGAGG ACGAGACGAG GGGGCC ATG GCT CAG        115
                                                Met Ala Gln
                                                    815
```

| | | | | | | | | | | | | | | | | |
|---|---|---|---|---|---|---|---|---|---|---|---|---|---|---|---|---|
| ATC | TTG | CTC | CAC | GGC | ACG | CTC | CAC | GCC | ACC | ATC | TTC | GAG | GCC | GAG | TCG | 163 |
| Ile | Leu | Leu | His | Gly | Thr | Leu | His | Ala | Thr | Ile | Phe | Glu | Ala | Glu | Ser | |
| | | | | 820 | | | | | 825 | | | | | 830 | | |
| CTC | TCC | AAC | CCG | CAC | CGC | GCC | ACT | GGC | GGC | GCC | CCC | AAG | TTC | ATC | CGC | 211 |
| Leu | Ser | Asn | Pro | His | Arg | Ala | Thr | Gly | Gly | Ala | Pro | Lys | Phe | Ile | Arg | |
| | | | 835 | | | | | 840 | | | | | 845 | | | |
| AAG | CTT | GTG | GAA | GGG | ATC | GAG | GAC | ACC | GTG | GGT | GTC | GGC | AAG | GGC | GCC | 259 |
| Lys | Leu | Val | Glu | Gly | Ile | Glu | Asp | Thr | Val | Gly | Val | Gly | Lys | Gly | Ala | |
| | | 850 | | | | | 855 | | | | | 860 | | | | |
| ACC | AAG | ATA | TAT | GCC | ACC | GTC | GAT | CTC | GAG | AAG | GCC | CGT | GTC | GGG | CGG | 307 |
| Thr | Lys | Ile | Tyr | Ala | Thr | Val | Asp | Leu | Glu | Lys | Ala | Arg | Val | Gly | Arg | |
| | 865 | | | | | 870 | | | | | 875 | | | | | |
| ACC | CGG | ATG | ATC | TCC | AAC | GAG | CCC | GTG | AAC | CCT | CGT | TGG | TAC | GAG | TCC | 355 |
| Thr | Arg | Met | Ile | Ser | Asn | Glu | Pro | Val | Asn | Pro | Arg | Trp | Tyr | Glu | Ser | |
| 880 | | | | | 885 | | | | | 890 | | | | | 895 | |
| TTC | CAC | ATC | TAC | TGC | GCG | CAC | ATG | GCC | GCC | GAC | GTC | ATC | TTC | ACC | GTC | 403 |
| Phe | His | Ile | Tyr | Cys | Ala | His | Met | Ala | Ala | Asp | Val | Ile | Phe | Thr | Val | |
| | | | | 900 | | | | 905 | | | | | 910 | | | |
| AAG | ATC | GAC | AAC | TCC | ATC | GGG | GCC | TCG | CTC | ATC | GGG | AGG | GCC | TAC | TTG | 451 |
| Lys | Ile | Asp | Asn | Ser | Ile | Gly | Ala | Ser | Leu | Ile | Gly | Arg | Ala | Tyr | Leu | |
| | | | 915 | | | | | 920 | | | | | 925 | | | |
| GCT | GTC | CAG | GAC | CTC | CTG | GGA | GGG | GAG | GAG | ATC | GAC | AAG | TGG | CTT | GAA | 499 |
| Ala | Val | Gln | Asp | Leu | Leu | Gly | Gly | Glu | Glu | Ile | Asp | Lys | Trp | Leu | Glu | |
| | | 930 | | | | | 935 | | | | | 940 | | | | |
| ATC | TCC | GAT | GAA | AAT | CGT | GAG | CCT | GTT | GGG | GAC | AGC | AAG | ATC | CAT | GTG | 547 |
| Ile | Ser | Asp | Glu | Asn | Arg | Glu | Pro | Val | Gly | Asp | Ser | Lys | Ile | His | Val | |
| | 945 | | | | | 950 | | | | | 955 | | | | | |
| AAG | CTC | CAG | TAC | TTT | GAC | GTC | GGC | AAG | GAC | CGT | AAC | TGG | GCG | AGG | GGT | 595 |
| Lys | Leu | Gln | Tyr | Phe | Asp | Val | Gly | Lys | Asp | Arg | Asn | Trp | Ala | Arg | Gly | |
| 960 | | | | | 965 | | | | | 970 | | | | | 975 | |
| GTC | CGG | AGC | ACC | AAG | TAC | CCT | GGT | GTC | CCT | TAC | ACC | TTC | TTC | TCG | CAG | 643 |
| Val | Arg | Ser | Thr | Lys | Tyr | Pro | Gly | Val | Pro | Tyr | Thr | Phe | Phe | Ser | Gln | |
| | | | | 980 | | | | | 985 | | | | | 990 | | |
| AGG | CAG | GGG | TGT | AAG | GTT | ACT | CTG | TAC | CAG | GAC | GCT | CAT | GTG | CCG | GAC | 691 |
| Arg | Gln | Gly | Cys | Lys | Val | Thr | Leu | Tyr | Gln | Asp | Ala | His | Val | Pro | Asp | |
| | | | 995 | | | | | 1000 | | | | | 1005 | | | |
| AAC | TTT | GTT | CCC | AGG | ATC | CAG | CTC | GCT | GAT | GGC | AAG | AAC | TAT | GAG | CCG | 739 |
| Asn | Phe | Val | Pro | Arg | Ile | Gln | Leu | Ala | Asp | Gly | Lys | Asn | Tyr | Glu | Pro | |
| | | 1010 | | | | | 1015 | | | | | 1020 | | | | |
| CAC | AGG | TGC | TGG | GAG | GAT | ATC | TTT | GAT | GCT | ATA | AGC | AAG | GCT | CAG | CAT | 787 |
| His | Arg | Cys | Trp | Glu | Asp | Ile | Phe | Asp | Ala | Ile | Ser | Lys | Ala | Gln | His | |
| | 1025 | | | | | 1030 | | | | | 1035 | | | | | |
| TTG | ATT | TAC | ATC | ACT | GGC | TGG | TCC | GTG | TAC | ACA | GAG | ATC | ACC | TTG | GTC | 835 |
| Leu | Ile | Tyr | Ile | Thr | Gly | Trp | Ser | Val | Tyr | Thr | Glu | Ile | Thr | Leu | Val | |
| 1040 | | | | | 1045 | | | | | 1050 | | | | | 1055 | |
| AGG | GAC | ACC | AAC | AGG | CCA | AAA | CCT | GGT | GGT | GAT | GTT | ACT | CTT | GGG | GAG | 883 |
| Arg | Asp | Thr | Asn | Arg | Pro | Lys | Pro | Gly | Gly | Asp | Val | Thr | Leu | Gly | Glu | |
| | | | | 1060 | | | | | 1065 | | | | | 1070 | | |
| TTG | CTC | AAG | AGG | AAG | GCC | AGT | GAA | GGT | GTC | CGG | GTG | CTT | ATG | CTG | GTG | 931 |
| Leu | Leu | Lys | Arg | Lys | Ala | Ser | Glu | Gly | Val | Arg | Val | Leu | Met | Leu | Val | |
| | | | 1075 | | | | | 1080 | | | | | 1085 | | | |
| TGG | GAT | GAC | AGG | ACT | TCT | GTC | GGC | CTG | CTT | AAG | AAG | GAT | GGC | TTG | ATG | 979 |
| Trp | Asp | Asp | Arg | Thr | Ser | Val | Gly | Leu | Leu | Lys | Lys | Asp | Gly | Leu | Met | |
| | | | 1090 | | | | | 1095 | | | | | 1100 | | | |
| GCT | ACC | CAT | GAT | GAG | GAG | ACT | GCA | AAT | TAC | TTC | CAT | GGC | ACG | GAT | GTC | 1027 |
| Ala | Thr | His | Asp | Glu | Glu | Thr | Ala | Asn | Tyr | Phe | His | Gly | Thr | Asp | Val | |
| | | 1105 | | | | | 1110 | | | | | 1115 | | | | |
| AAC | TGT | GTT | CTG | TGC | CCT | CGC | AAC | CCT | GAT | GAT | TCT | GGC | AGC | TTT | GTC | 1075 |
| Asn | Cys | Val | Leu | Cys | Pro | Arg | Asn | Pro | Asp | Asp | Ser | Gly | Ser | Phe | Val | |
| 1120 | | | | | 1125 | | | | | 1130 | | | | | 1135 | |

```
CAG GAT CTG CAG ATA TCA ACT ATG TTC ACG CAC CAC CAG AAG ATA GTA        1123
Gln Asp Leu Gln Ile Ser Thr Met Phe Thr His His Gln Lys Ile Val
            1140                1145                1150

GTA GTC GAC CAT GAG ATG CCG AAC CAG GGA TCC CAG CAA AGG AGG ATA        1171
Val Val Asp His Glu Met Pro Asn Gln Gly Ser Gln Gln Arg Arg Ile
            1155                1160                1165

GTC AGC TTC ATT GGT GGC ATT GAC CTT TGT GAT GGA AGA TAT GAT ACC        1219
Val Ser Phe Ile Gly Gly Ile Asp Leu Cys Asp Gly Arg Tyr Asp Thr
            1170                1175                1180

CAG TAC CAC TCC TTG TTC AGG ACG CTT GAC ACT GTC CAT CAC GAT GAC        1267
Gln Tyr His Ser Leu Phe Arg Thr Leu Asp Thr Val His His Asp Asp
            1185                1190                1195

TTC CAC CAG CCG AAC TTT GAG GGT GGG TCA ATC AAG AAA GGT GGC CCA        1315
Phe His Gln Pro Asn Phe Glu Gly Gly Ser Ile Lys Lys Gly Gly Pro
1200                1205                1210                1215

AGG GAG CCA TGG CAT GAT ATC CAC TCA CGG TTG GAA GGG CCA ATC GCT        1363
Arg Glu Pro Trp His Asp Ile His Ser Arg Leu Glu Gly Pro Ile Ala
            1220                1225                1230

TGG GAT GTT CTT TAC AAC TTT GAG CAG AGA TGG AGA AAG CAG GGT GGT        1411
Trp Asp Val Leu Tyr Asn Phe Glu Gln Arg Trp Arg Lys Gln Gly Gly
            1235                1240                1245

AAG GAC CTC CTT GTG CGT CTC AGG GAT CTT CCT GAC ATT ATC ATC CCC        1459
Lys Asp Leu Leu Val Arg Leu Arg Asp Leu Pro Asp Ile Ile Ile Pro
            1250                1255                1260

CCT TCT CCT GTG ATG TTC CCG GAG GAC AGA GAG ACA TGG AAT GTT CAG        1507
Pro Ser Pro Val Met Phe Pro Glu Asp Arg Glu Thr Trp Asn Val Gln
            1265                1270                1275

CTC TTC AGA TCC ATC GAT GGT GGT GCT GCT TTT GGC TTC CCC GAG ACT        1555
Leu Phe Arg Ser Ile Asp Gly Gly Ala Ala Phe Gly Phe Pro Glu Thr
1280                1285                1290                1295

CCC GAG GAA GCT GCA AGA GCT GGG CTT GTG AGT GGA AAG GAT CAA ATC        1603
Pro Glu Glu Ala Ala Arg Ala Gly Leu Val Ser Gly Lys Asp Gln Ile
            1300                1305                1310

ATC GAC CGG AGT ATC CAG GAT GCA TAC GTA AAC GCC ATA CGG AGG GCG        1651
Ile Asp Arg Ser Ile Gln Asp Ala Tyr Val Asn Ala Ile Arg Arg Ala
            1315                1320                1325

AAG AAC TTC ATC TAC ATT GAG AAT CAG TAC TTC CTT GGA AGT TCA TAC        1699
Lys Asn Phe Ile Tyr Ile Glu Asn Gln Tyr Phe Leu Gly Ser Ser Tyr
            1330                1335                1340

GGC TGG AAG CCC GAA GGC ATC AAG CCG GAA GAA ATC GGT GCT CTT CAC        1747
Gly Trp Lys Pro Glu Gly Ile Lys Pro Glu Glu Ile Gly Ala Leu His
            1345                1350                1355

TTG ATT CCG AAG GAG CTC TCG CTG AAG ATT GTC AGC AAG ATT GAA GCT        1795
Leu Ile Pro Lys Glu Leu Ser Leu Lys Ile Val Ser Lys Ile Glu Ala
1360                1365                1370                1375

GGG GAG CGG TTT ACT GTT TAT GTT GTG GTG CCA ATG TGG CCT GAG GGT        1843
Gly Glu Arg Phe Thr Val Tyr Val Val Val Pro Met Trp Pro Glu Gly
            1380                1385                1390

GTT CCA GAA AGC GCT TCT GTT CAG GCA ATC CTT GAC TGG CAA AGG AGA        1891
Val Pro Glu Ser Ala Ser Val Gln Ala Ile Leu Asp Trp Gln Arg Arg
            1395                1400                1405

ACG ATG GAG ATG ATG TAC ACT GAC ATC GCA CAA GCT CTC GAA GCC AAC        1939
Thr Met Glu Met Met Tyr Thr Asp Ile Ala Gln Ala Leu Glu Ala Asn
            1410                1415                1420

GGG ATT GAA GCA AAC CCC AAG GAC TAT CTC ACT TTC TTC TGC TTA GGT        1987
Gly Ile Glu Ala Asn Pro Lys Asp Tyr Leu Thr Phe Phe Cys Leu Gly
            1425                1430                1435

AAC CGT GAG GTA AAG CAG GAG GGA GAA TAT GAA CCA GAG GAG CAC CCA        2035
Asn Arg Glu Val Lys Gln Glu Gly Glu Tyr Glu Pro Glu Glu His Pro
1440                1445                1450                1455
```

| | | |
|---|---|---|
| GAA CCT GAC ACT GAT TAC ATC CGG GCT CAA GAG GCT AGG AGG TTT ATG<br>Glu Pro Asp Thr Asp Tyr Ile Arg Ala Gln Glu Ala Arg Arg Phe Met<br>　　　1460　　　　　　　　　1465　　　　　　　　　1470 | | 2083 |
| ATC TAT GTT CAT ACC AAA ATG ATG ATA GTG GAC GAC GAG TAC ATC ATC<br>Ile Tyr Val His Thr Lys Met Met Ile Val Asp Asp Glu Tyr Ile Ile<br>　　　　　　1475　　　　　　　　　1480　　　　　　　　　1485 | | 2131 |
| ATT GGG TCC GCC AAC ATC AAC CAG AGG TCC ATG GAC GGT GCC AGG GAC<br>Ile Gly Ser Ala Asn Ile Asn Gln Arg Ser Met Asp Gly Ala Arg Asp<br>　　　1490　　　　　　　　　1495　　　　　　　　　1500 | | 2179 |
| TCC GAG ATC GCC ATG GGC GCG TAC CAG CCG TAC CAC TTG GCG ACT AGG<br>Ser Glu Ile Ala Met Gly Ala Tyr Gln Pro Tyr His Leu Ala Thr Arg<br>　　　1505　　　　　　　　　1510　　　　　　　　　1515 | | 2227 |
| CAG CCT GCC CGG GGC CAG ATC CAT GGC TTC CGG ATG TCT CTT TGG TAC<br>Gln Pro Ala Arg Gly Gln Ile His Gly Phe Arg Met Ser Leu Trp Tyr<br>1520　　　　　　　　　1525　　　　　　　　　1530　　　　　　　　　1535 | | 2275 |
| GAG CAC CTG GGA ATG CTG GAA GAC GTC TTC CAG CGG CCC GAG AGC GTA<br>Glu His Leu Gly Met Leu Glu Asp Val Phe Gln Arg Pro Glu Ser Val<br>　　　　　　1540　　　　　　　　　1545　　　　　　　　　1550 | | 2323 |
| GAG TGT GTG CAG AAG GTG AAC GAG GTC GCC GAG AAG TAC TGG GAC CTG<br>Glu Cys Val Gln Lys Val Asn Glu Val Ala Glu Lys Tyr Trp Asp Leu<br>　　　1555　　　　　　　　　1560　　　　　　　　　1565 | | 2371 |
| TAC TCG AGC GAC GAC CTG GAG CAG GAC CTC CCG GGC CAC CTC CTC AGC<br>Tyr Ser Ser Asp Asp Leu Glu Gln Asp Leu Pro Gly His Leu Leu Ser<br>　　　1570　　　　　　　　　1575　　　　　　　　　1580 | | 2419 |
| TAC CCG ATC GGT GTC ACT GCC GAC GGC AGC GTT ACC GAG CTG CCC GGG<br>Tyr Pro Ile Gly Val Thr Ala Asp Gly Ser Val Thr Glu Leu Pro Gly<br>　　　1585　　　　　　　　　1590　　　　　　　　　1595 | | 2467 |
| ATG GAG AAC TTC CCC GAC ACC CGC GCC CGC GTC CTC GGG AAC AAG TCG<br>Met Glu Asn Phe Pro Asp Thr Arg Ala Arg Val Leu Gly Asn Lys Ser<br>1600　　　　　　　　　1605　　　　　　　　　1610　　　　　　　　　1615 | | 2515 |
| GAT TAC CTC CCG CCC ATC CTC ACC ACA TAGAGTGCAC ACTGCAGGCA<br>Asp Tyr Leu Pro Pro Ile Leu Thr Thr<br>　　　　　　1620 | | 2562 |
| GCGCCATGGC TGCTCTCCTC TCTGGCCTCA CCTTGGTGTC CCTGTGTTTG TGTTTGGGAC | | 2622 |
| ACTGGAGGTT CAGATTGCAG TGTTGATATT ATATCCCCCC TCCGTCCAGA GGGATTCGAC | | 2682 |
| GTTATTGAGT CATAATAAAA TGCATTGTGC ACGGTGGGAG ACTGGGAGGA TAGGAATTAT | | 2742 |
| AGTTGTTTAT TACAGTACGA CTGCTTACTG CATCCAGATT GTGTTGTCCC TAAAAAAAAA | | 2802 |
| AA | | 2804 |

( 2 ) INFORMATION FOR SEQ ID NO:4:

( i ) SEQUENCE CHARACTERISTICS:
　　　　　　( A ) LENGTH: 812 amino acids
　　　　　　( B ) TYPE: amino acid
　　　　　　( D ) TOPOLOGY: linear ( i i ) MOLECULE TYPE: protein ( x i ) SEQUENCE DESCRIPTION: SEQ ID NO:4:

Met Ala Gln Ile Leu Leu His Gly Thr Leu His Ala Thr Ile Phe Glu
 1               5                  10                  15

Ala Glu Ser Leu Ser Asn Pro His Arg Ala Thr Gly Gly Ala Pro Lys
                20                  25                  30

Phe Ile Arg Lys Leu Val Glu Gly Ile Glu Asp Thr Val Gly Val Gly
            35                  40                  45

Lys Gly Ala Thr Lys Ile Tyr Ala Thr Val Asp Leu Glu Lys Ala Arg
        50                  55                  60

Val Gly Arg Thr Arg Met Ile Ser Asn Glu Pro Val Asn Pro Arg Trp
65                  70                  75                  80

```
Tyr Glu Ser Phe His Ile Tyr Cys Ala His Met Ala Ala Asp Val Ile
                 85                  90                  95
Phe Thr Val Lys Ile Asp Asn Ser Ile Gly Ala Ser Leu Ile Gly Arg
                100                 105                 110
Ala Tyr Leu Ala Val Gln Asp Leu Leu Gly Gly Glu Ile Asp Lys
            115                 120                 125
Trp Leu Glu Ile Ser Asp Glu Asn Arg Glu Pro Val Gly Asp Ser Lys
            130                 135                 140
Ile His Val Lys Leu Gln Tyr Phe Asp Val Gly Lys Asp Arg Asn Trp
145                 150                 155                 160
Ala Arg Gly Val Arg Ser Thr Lys Tyr Pro Gly Val Pro Tyr Thr Phe
                165                 170                 175
Phe Ser Gln Arg Gln Gly Cys Lys Val Thr Leu Tyr Gln Asp Ala His
                180                 185                 190
Val Pro Asp Asn Phe Val Pro Arg Ile Gln Leu Ala Asp Gly Lys Asn
            195                 200                 205
Tyr Glu Pro His Arg Cys Trp Glu Asp Ile Phe Asp Ala Ile Ser Lys
    210                 215                 220
Ala Gln His Leu Ile Tyr Ile Thr Gly Trp Ser Val Tyr Thr Glu Ile
225                 230                 235                 240
Thr Leu Val Arg Asp Thr Asn Arg Pro Lys Pro Gly Gly Asp Val Thr
                245                 250                 255
Leu Gly Glu Leu Leu Lys Arg Lys Ala Ser Glu Gly Val Arg Val Leu
                260                 265                 270
Met Leu Val Trp Asp Asp Arg Thr Ser Val Gly Leu Leu Lys Lys Asp
            275                 280                 285
Gly Leu Met Ala Thr His Asp Glu Glu Thr Ala Asn Tyr Phe His Gly
    290                 295                 300
Thr Asp Val Asn Cys Val Leu Cys Pro Arg Asn Pro Asp Asp Ser Gly
305                 310                 315                 320
Ser Phe Val Gln Asp Leu Gln Ile Ser Thr Met Phe Thr His His Gln
                325                 330                 335
Lys Ile Val Val Val Asp His Glu Met Pro Asn Gln Gly Ser Gln Gln
            340                 345                 350
Arg Arg Ile Val Ser Phe Ile Gly Gly Ile Asp Leu Cys Asp Gly Arg
        355                 360                 365
Tyr Asp Thr Gln Tyr His Ser Leu Phe Arg Thr Leu Asp Thr Val His
    370                 375                 380
His Asp Asp Phe His Gln Pro Asn Phe Glu Gly Gly Ser Ile Lys Lys
385                 390                 395                 400
Gly Gly Pro Arg Glu Pro Trp His Asp Ile His Ser Arg Leu Glu Gly
                405                 410                 415
Pro Ile Ala Trp Asp Val Leu Tyr Asn Phe Glu Gln Arg Trp Arg Lys
            420                 425                 430
Gln Gly Gly Lys Asp Leu Leu Val Arg Leu Arg Asp Leu Pro Asp Ile
        435                 440                 445
Ile Ile Pro Pro Ser Pro Val Met Phe Pro Glu Asp Arg Glu Thr Trp
    450                 455                 460
Asn Val Gln Leu Phe Arg Ser Ile Asp Gly Gly Ala Ala Phe Gly Phe
465                 470                 475                 480
Pro Glu Thr Pro Glu Glu Ala Ala Arg Ala Gly Leu Val Ser Gly Lys
                485                 490                 495
Asp Gln Ile Ile Asp Arg Ser Ile Gln Asp Ala Tyr Val Asn Ala Ile
```

|     |     |     | 500 |     |     |     |     | 505 |     |     |     |     | 510 |     |
| --- | --- | --- | --- | --- | --- | --- | --- | --- | --- | --- | --- | --- | --- | --- |
| Arg | Arg | Ala | Lys | Asn | Phe | Ile | Tyr | Ile | Glu | Asn | Gln | Tyr | Phe | Leu | Gly |
|     |     |     | 515 |     |     |     |     | 520 |     |     |     |     | 525 |     |     |
| Ser | Ser | Tyr | Gly | Trp | Lys | Pro | Glu | Gly | Ile | Lys | Pro | Glu | Glu | Ile | Gly |
|     |     |     | 530 |     |     |     | 535 |     |     |     |     | 540 |     |     |     |
| Ala | Leu | His | Leu | Ile | Pro | Lys | Glu | Leu | Ser | Leu | Lys | Ile | Val | Ser | Lys |
| 545 |     |     |     |     | 550 |     |     |     |     | 555 |     |     |     |     | 560 |
| Ile | Glu | Ala | Gly | Glu | Arg | Phe | Thr | Val | Tyr | Val | Val | Pro | Met | Trp |
|     |     |     |     |     | 565 |     |     |     | 570 |     |     |     |     | 575 |
| Pro | Glu | Gly | Val | Pro | Glu | Ser | Ala | Ser | Val | Gln | Ala | Ile | Leu | Asp | Trp |
|     |     |     | 580 |     |     |     |     | 585 |     |     |     |     | 590 |     |     |
| Gln | Arg | Arg | Thr | Met | Glu | Met | Met | Tyr | Thr | Asp | Ile | Ala | Gln | Ala | Leu |
|     |     | 595 |     |     |     |     | 600 |     |     |     |     | 605 |     |     |     |
| Glu | Ala | Asn | Gly | Ile | Glu | Ala | Asn | Pro | Lys | Asp | Tyr | Leu | Thr | Phe | Phe |
|     | 610 |     |     |     |     | 615 |     |     |     |     | 620 |     |     |     |     |
| Cys | Leu | Gly | Asn | Arg | Glu | Val | Lys | Gln | Glu | Gly | Glu | Tyr | Glu | Pro | Glu |
| 625 |     |     |     |     | 630 |     |     |     |     | 635 |     |     |     |     | 640 |
| Glu | His | Pro | Glu | Pro | Asp | Thr | Asp | Tyr | Ile | Arg | Ala | Gln | Glu | Ala | Arg |
|     |     |     |     | 645 |     |     |     |     | 650 |     |     |     |     | 655 |     |
| Arg | Phe | Met | Ile | Tyr | Val | His | Thr | Lys | Met | Met | Ile | Val | Asp | Asp | Glu |
|     |     |     | 660 |     |     |     |     | 665 |     |     |     |     | 670 |     |     |
| Tyr | Ile | Ile | Ile | Gly | Ser | Ala | Asn | Ile | Asn | Gln | Arg | Ser | Met | Asp | Gly |
|     |     | 675 |     |     |     |     | 680 |     |     |     |     | 685 |     |     |     |
| Ala | Arg | Asp | Ser | Glu | Ile | Ala | Met | Gly | Ala | Tyr | Gln | Pro | Tyr | His | Leu |
|     | 690 |     |     |     |     | 695 |     |     |     |     | 700 |     |     |     |     |
| Ala | Thr | Arg | Gln | Pro | Ala | Arg | Gly | Gln | Ile | His | Gly | Phe | Arg | Met | Ser |
| 705 |     |     |     |     | 710 |     |     |     |     | 715 |     |     |     |     | 720 |
| Leu | Trp | Tyr | Glu | His | Leu | Gly | Met | Leu | Glu | Asp | Val | Phe | Gln | Arg | Pro |
|     |     |     |     | 725 |     |     |     |     | 730 |     |     |     |     | 735 |     |
| Glu | Ser | Val | Glu | Cys | Val | Gln | Lys | Val | Asn | Glu | Val | Ala | Glu | Lys | Tyr |
|     |     |     | 740 |     |     |     |     | 745 |     |     |     |     | 750 |     |     |
| Trp | Asp | Leu | Tyr | Ser | Ser | Asp | Leu | Glu | Gln | Asp | Leu | Pro | Gly | His |
|     |     | 755 |     |     |     | 760 |     |     |     | 765 |     |     |     |     |
| Leu | Leu | Ser | Tyr | Pro | Ile | Gly | Val | Thr | Ala | Asp | Gly | Ser | Val | Thr | Glu |
|     | 770 |     |     |     |     | 775 |     |     |     |     | 780 |     |     |     |     |
| Leu | Pro | Gly | Met | Glu | Asn | Phe | Pro | Asp | Thr | Arg | Ala | Arg | Val | Leu | Gly |
| 785 |     |     |     |     | 790 |     |     |     |     | 795 |     |     |     |     | 800 |
| Asn | Lys | Ser | Asp | Tyr | Leu | Pro | Pro | Ile | Leu | Thr | Thr |
|     |     |     |     | 805 |     |     |     |     | 810 |     |     |

(2) INFORMATION FOR SEQ ID NO:5:

(i) SEQUENCE CHARACTERISTICS:
        (A) LENGTH: 2799 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1876..1983

(ix) FEATURE:
        (A) NAME/KEY: CDS
        (B) LOCATION: 2524..2799

(xi) SEQUENCE DESCRIPTION: SEQ ID NO:5:

```
CAAGGGTGTA CATAGATTTG TCTCGTAAAA TAGTATTATA ATATTATAAA CTTATTACTC      60
TATCCGTTCT AAAATATAAG AACCTTATGA CTGGATGGAA CATTTCCTAG TACTACGAAT     120
CTGAACACAT GTCTAGATTC ATAGTACTAG GAAATGTCTC ATCGCGGTAC TAGGTTCTTA     180
TATTTTAGGA TGGAGGGAGT TTAATATAAA ACTAATGGTT AGAACTTTGA AAGTTTGATT     240
TTAAATGTCA AATATTTATG GCTGGAGGTA GTATAATATG TTTTTTTGG  GACGTAGACT     300
AGGTAGTATA ATATGTTTGG TTGTGTTTAG ATCCAATATT TGGATCCAAA CTTCAGTCAT     360
TTTCCATCAC ATCAACTTGT CATATACACA TAACTTTTCA GTCACATCAT CCCCAATTTC     420
AACCAAAATC AAACTTTGCG CTGAACTAAA CACAACCTTT GGGCCCGTTT AGTTCCCCAA     480
TTTTTTTCCC AAAAACATCA CATCGAATCT TTGGACACAT GCATGAAGCA TTAAATATAG     540
ATAAAAAGAA AAACTAATTG CACAGTTATG GAGGAAATCG CGAGACGAAT CTTTTAAGCC     600
TAATTAGTCC GTGATTAGCC ATAAGTGCTA CAGTAACCCA ATTGTGCTAA TGACGGCTTA     660
ATTAGTCTCC ACAAGATTCG TCTCGCAGTT TCCAGGCGAG TTCTGAAATT AGTTTTTTCA     720
TTCGTGTCCG AAAACCCCTT CCGACATCCG GTCAAACGTT CGATATGACA CCCACAAATT     780
TTCTTTTCCC CAACTAAACA CACCCTTTAT CTCTTACCCT CTGGCTCTTT CAGTAGGCAT     840
ATCCAAGACA GCTGGTAATG CAGGCTCGGA CATAATTTGA CAGTTACGTT CATGTGACCG     900
ACGGTTGATG CTAGTGCAAC TGCAACATAC TGTTCAGATG GATGTCCCAA CGAGCTCAAA     960
ACAACTTAGG TGGCGCGTCG CGATTCATCA ATAACTCAAA TGGAAGCGCA AGTGCACGTA    1020
CGAAAATGAC AGCGAGTGAG GTGGCGAGCC TCACCTTGGT GATCCCAACC GGATAAGCTA    1080
TGCATCAGCC AGTTTCGTGG GGCTGCACAT TCGTCGAAC  ACCTGGAGTC CACGCCGCCG    1140
GCGACGTCGG CACAGCGCGC CCGCCCACCG CCCACGCACG CGCTTGACTC CACCCATGTT    1200
CTCCCTTCTC GACGCCCGCG AAGCCAGCGA ACCGATCCGA GGAAGTCAAG CCCCCACCGC    1260
CACTTGGACC GACCTCGGGA CGACGACGCC CCCGCGCTCT CTAGACGCG  CGGACGACGC    1320
GGGCGCTGGC TCCGCGACGC GACGTCGCGG TCATGGAGTA ACCGCGACGG ACAGATACTT    1380
CTACCCGTTT TTAACCTCGC CTCCTCCTCC TCCCGGCTCG AGATCCGTGG CCACGACGCG    1440
TGGTGGGAAA CCGGGAACGA CGTGCACGCA CGCACACAGG GCAAGTTTCA GTAGAAAAAT    1500
CGCCGGCATC CAGATCGGGA CAGTCTCTCT TCTCCCGCAA TTTTATAATC TCGCTCGATC    1560
CAATCTGCTC CCCTTCTTCT TCTACTCTCC CCATCTCGGC TCTCGCCATC GCCATCCTCC    1620
TCTCCCTTCC CGGAGAAGAC GCCTCCCTCC GCCGATCACC ACCCGGTAAG CCCAGTGTGC    1680
TTAGGCTAAG CGCACTAGAG CTTCTTGCTC GCTTGCTTCT TCTCCGCTCA GATCTGCTTG    1740
CTTGCTTGCT TCGCTAGAAC CCTACTCTGT GCTGCGAGTG TCGCTGCTTC GTCTTCCTTC    1800
CTCAAGTTCG ATCTGATTGT GTGTGTGGGG GGGCGCAGGT AGGGCGAGGA GGGAGCCAAA    1860
TCCAAATCAG CAGCC ATG GCG CAG ATG CTG CTC CAT GGG ACG CTG CAC GCC    1911
                 Met Ala Gln Met Leu Leu His Gly Thr Leu His Ala
                                 815                 820
ACC ATC TTC GAG GCG GCG TCG CTC TCC AAC CCG CAC CGC GCC AGC GGA    1959
Thr Ile Phe Glu Ala Ala Ser Leu Ser Asn Pro His Arg Ala Ser Gly
825             830                 835                     840
AGC GCC CCC AAG TTC ATC CGC AAG GTTCGGACCC TTCTCCTTAA CTACTCGTC    2013
Ser Ala Pro Lys Phe Ile Arg Lys
                845
TTTGCTCTTG CTCTTTTTCT TTTGTGTCCC TTTCTTGTGT GTGCGTTTGC ATGAGCCCGA    2073
ATTTGATCTG CTAGTGCACA GTACAGTCAG ATACACTGAA ACGATCTGGA AATTCTGGAT    2133
TATTAGGAAA AATAAAGAGG TAGTAGACAA GAATTGGAGA TACTTTCTAT CAAGATTGGT    2193
```

```
CTATTATGCT TGGCCATTTC TTGTTTGACC CAAGTACTTC TTTGAATCTA GAGTTTGCTG         2253

TGTGTGATGT GGTGTGTGTT TGTGTCACCA AAAATCTTCA TTAGCTAAAA CTGAAATTTT         2313

ATTTATTAAC TGACCTACTA AAAATGTAGA GTTCTCTGTG TGTGATGTGT GCTTGTGTCA         2373

CCAAAAATCT TGATTTGATA GAGTTTTTAT TTATTTATTA ACTGACCTAC TACAAATCTA         2433

TTGCTGTATG CTATGTGTGT CTGTATCACC TGAAATGCAA TGTCTTCTTC TTTGTTGTTC         2493

TTGATCTAAC ACGTGAGCTC ATGTCAACAG TTT GTG GAG GGG ATT GAG GAC ACT         2547
                                 Phe Val Glu Gly Ile Glu Asp Thr
                                  1               5

GTG GGT GTC GGC AAA GGC GCC ACC AAG GTG TAT TCT ACC ATT GAT CTG           2595
Val Gly Val Gly Lys Gly Ala Thr Lys Val Tyr Ser Thr Ile Asp Leu
        10              15              20

GAG AAA GCT CGT GTA GGG CGA ACT AGG ATG ATA ACC AAT GAG CCC ATC           2643
Glu Lys Ala Arg Val Gly Arg Thr Arg Met Ile Thr Asn Glu Pro Ile
 25              30              35              40

AAC CCT CGC TGG TAT GAG TCG TTC CAC ATC TAT TGC GCT CAT ATG GCT           2691
Asn Pro Arg Trp Tyr Glu Ser Phe His Ile Tyr Cys Ala His Met Ala
                45              50              55

TCC AAT GTG ATC TTC ACT GTC AAG ATT GAT AAC CCT ATT GGG GCA ACG           2739
Ser Asn Val Ile Phe Thr Val Lys Ile Asp Asn Pro Ile Gly Ala Thr
            60              65              70

AAT ATT GGG AGG GCT TAC CTG CCT GTC CAA GAG CTT CTC AAT GGA GAG           2787
Asn Ile Gly Arg Ala Tyr Leu Pro Val Gln Glu Leu Leu Asn Gly Glu
        75              80              85

GAG ATT GAC AGA                                                           2799
Glu Ile Asp Arg
        90
```

( 2 ) INFORMATION FOR SEQ ID NO:6:

( i ) SEQUENCE CHARACTERISTICS:
        ( A ) LENGTH: 36 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Ala Gln Met Leu Leu His Gly Thr Leu His Ala Thr Ile Phe Glu
 1               5                  10                  15

Ala Ala Ser Leu Ser Asn Pro His Arg Ala Ser Gly Ser Ala Pro Lys
                20                  25                  30

Phe Ile Arg Lys
        35
```

( 2 ) INFORMATION FOR SEQ ID NO:7:

( i ) SEQUENCE CHARACTERISTICS:
        ( A ) LENGTH: 92 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Phe Val Glu Gly Ile Glu Asp Thr Val Gly Val Gly Lys Gly Ala Thr
 1               5                  10                  15

Lys Val Tyr Ser Thr Ile Asp Leu Glu Lys Ala Arg Val Gly Arg Thr
                20                  25                  30

Arg Met Ile Thr Asn Glu Pro Ile Asn Pro Arg Trp Tyr Glu Ser Phe
                35                  40                  45
```

| | | | | | | | | | | | | | | |
|---|---|---|---|---|---|---|---|---|---|---|---|---|---|---|
| His | Ile | Tyr | Cys | Ala | His | Met | Ala | Ser | Asn | Val | Ile | Phe | Thr | Val Lys |
| | 50 | | | | | 55 | | | | | 60 | | | |
| Ile | Asp | Asn | Pro | Ile | Gly | Ala | Thr | Asn | Ile | Gly | Arg | Ala | Tyr | Leu Pro |
| 65 | | | | | 70 | | | | | 75 | | | | 80 |
| Val | Gln | Glu | Leu | Leu | Asn | Gly | Glu | Glu | Ile | Asp | Arg | | | |
| | | | | 85 | | | | | 90 | | | | | |